(12) United States Patent
Ding et al.

(10) Patent No.: US 8,846,671 B2
(45) Date of Patent: Sep. 30, 2014

(54) HETEROCYCLIC ALKYNYL BENZENE COMPOUNDS AND MEDICAL COMPOSITIONS AND USES THEREOF

(75) Inventors: Ke Ding, Guangdong (CN); Deping Wang, Guangdong (CN); Duanqing Pei, Guangdong (CN); Zhang Zhang, Guangdong (CN); Mengjie Shen, Guangdong (CN); Kun Luo, Guangdong (CN); Yubing Feng, Guangdong (CN)

(73) Assignee: Guangzhou Institute of Biomedicine and Health, Chinese Academy of Sciences, Guangzhou, Guangdong (CN)

( * ) Notice: Subject to any disclaimer, the term of this patent is extended or adjusted under 35 U.S.C. 154(b) by 3 days.

(21) Appl. No.: 13/807,678

(22) PCT Filed: Jun. 3, 2011

(86) PCT No.: PCT/CN2011/000935
§ 371 (c)(1),
(2), (4) Date: Mar. 22, 2013

(87) PCT Pub. No.: WO2012/000304
PCT Pub. Date: Jan. 5, 2012

(65) Prior Publication Data
US 2013/0196985 A1 Aug. 1, 2013

(30) Foreign Application Priority Data

Jul. 1, 2010 (CN) .......................... 2010 1 0216603

(51) Int. Cl.
*A61K 31/535* (2006.01)
*C07D 401/00* (2006.01)

(52) U.S. Cl.
USPC ........ 514/233.2; 514/275; 514/341; 546/272; 546/118; 544/331; 544/295

(58) Field of Classification Search
USPC ............... 514/233.2, 341, 275; 544/331, 295; 546/272.7, 118, 272
See application file for complete search history.

(56) References Cited

U.S. PATENT DOCUMENTS 5,358,948 A * 10/1994 Bradshaw et al. ....... 514/253.01
7,799,782 B2 * 9/2010 Munson et al. ............ 514/234.5

FOREIGN PATENT DOCUMENTS

| CN | 101885722 A | 11/2010 |
| WO | 2006/044823 A2 | 4/2006 |
| WO | 2007/075869 A2 | 7/2007 |

OTHER PUBLICATIONS

Berge et al., "Pharmaceutical Salts", Journal of Pharmaceutical Sciences, vol. 66, No. 1, Jan. 1977, pp. 1-19.
International Search Report received for PCT Patent Application No. PCT/CN2011/000935, mailed on Sep. 8, 2011, 8 pages (4 pages of English Translation and 4 pages of Original Search Report).
Cee et al., "Alkynylpyrimidine Amide Derivatives as Potent, Selective, and Orally Active Inhibitors of Tie-2 Kinase", Journal of Medicinal Chemistry, vol. 50, No. 4, Jan. 25, 2007, pp. 627-640.
Deng et al., "Broad Spectrum Alkynyl Inhibitors of T315I Bcr-Abl", Bioorganic & Medicinal Chemistry Letters, vol. 20, No. 14, May 19, 2010, pp. 4196-4200.
Huang et al., "Discovery of 3-[2-(Imidazo[1,2-b]pyridazin-3-yl)ethynyl]-4-methyl-N-{4-[(4-methylpiperazin-1-yl)methyl]-3-(trifluoromethyl)phenyl}benzamide (AP24534), a Potent, Orally Active Pan-Inhibitor of Breakpoint Cluster Region-Abelson (BCR-ABL) Kinase Including the T315I Gatekeeper Mutant", Journal of Medicinal Chemistry, vol. 53, No. 12, Jun. 1, 2010, pp. 4701-4719.
Kansal et al., "A Three Dimensional Pharmacophore Modeling for KDR and Tie-2 Receptor Tyrosine Kinase Inhibitors and Virtual Screening for New Multikinase Inhibitors", QSAR & Combinatorial Science, vol. 28, No. 10, Oct. 31, 2009, pp. 1130-1147.

* cited by examiner

*Primary Examiner* — Rei-tsang Shiao
(74) *Attorney, Agent, or Firm* — Morrison & Foerster LLP

(57) ABSTRACT

The heterocyclic alkynyl benzene compounds of formula (I), their pharmaceutically acceptable salts and stereoisomers thereof, as well as application in preparing drugs for preventing or treating tumors. The compounds can overcome the clinically induced resistance against Gleevec.

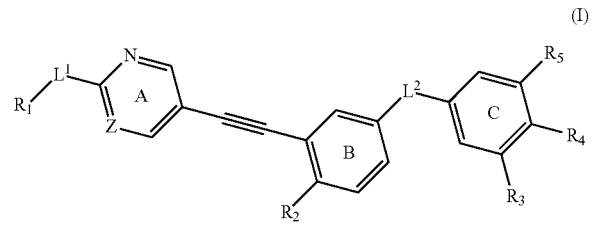

11 Claims, 8 Drawing Sheets

HETEROCYCLIC ALKYNYL BENZENE COMPOUNDS AND MEDICAL COMPOSITIONS AND USES THEREOF

CROSS REFERENCE TO RELATED APPLICATIONS

This application is a U.S. National Phase patent application of PCT/CN2011/000935, filed Jun. 3, 2011, which claims priority to Chinese application Serial No. CN201010216603.7, filed Jul. 1, 2010, all of which are hereby incorporated by reference in the present disclosure in their entirety.

FIELD OF THE INVENTION

The present invention relates to heterocyclic alkynyl benzene compounds of formula (I), their pharmaceutically acceptable salts and stereoisomers and prodrugs of formula (I), and their applications as the active ingredients for preparing drugs for preventing or treating tumors, particularly, to overcome the clinically induced resistance against Gleevec.

BACKGROUND OF THE INVENTION

Cancer is the $2^{nd}$ leading cause after cardiovascular diseases responsible for human death. Because of the environment pollution and other factors, the incidence of malignant tumor is increasing rapidly. Based on WHO's published data of 2003, there are over 100 million patients with malignant tumor in the world. About 6.2 millions patients with malignant tumor die for cancer which accounts for 12%~25% of the total death. It is estimated that the global new cases will reach 15 million per year in 2020. Recently, some novel anticancer drugs of protein tyrosine inhibitors have been developed and achieved great clinical benefits, however, it is still far away from meeting the growing clinical needs of cancer patients. Anticancer drug is still one of the most active areas in the worldwide drug development.

Molecular targeted cancer therapy is a strategy selectively killing tumor cells through chemical or biological approaches by interfering the key regulators of tumor cell growth. Comparing with the traditional cytotoxic drugs, molecular targeted therapy can selectively modulate key molecules which are closely related to tumor growth and treat patients with high specificity and selectivity, low toxicity and less side effects. It can also enhance the potency by combination with traditional chemotherapy and radiotherapy, and reduce the recurrence after surgery. Gleevec (STI571), the protein tyrosine kinase inhibitor, created a new era of molecular targeted therapy for cancer. The molecular targeted therapy has rapidly developed within these years. The emergence of molecular targeted therapy for cancer has impacted the traditional drug administration concepts and models. For example, because of its low toxicity and less side effects, targeted drugs usually do not reach dose-limited toxicity and maximum tolerated dose in the clinic trial phase I; satisfactory efficacy can be achieved without need for applying maximum tolerated dose for molecular targeted therapy drugs. Targeted cancer therapy is one of the hot issues and developmental tendency of cancer therapy.

Protein tyrosine kinases (PTKs) can phosphorylate the phenolic hydroxyl groups of tyrosine residues of many important proteins and further activate functions of functional proteins. There are over 520 protein kinases in human body, about half of which are protein tyrosine kinases (PTKs). These proteins play very important roles in the signal transduction pathways inside of cells and modulate a wide range of biological processes of cells including growth, differentiation, death, etc. Dysfunction of protein tyrosine kinase will cause a series of diseases. The studies show that half of protooncogenes and activation of oncogenes are related to protein tyrosine kinases. Abnormal expression of protein tyrosine kinase can cause disorder of cell proliferation regulation, and further cause tumors. In addition, abnormal expression of protein tyrosine kinase also closely relates to the tumor invasion and metastasis, the formation of new blood vessels, and resistance against chemotherapy drug. Novel protein tyrosine kinase inhibitor development has been one of the hottest issues in the world, and is also a focal point of all R&D institutions in all countries.

So far, over tens of small molecular inhibitors and antibodies of protein tyrosine kinase haven advanced into clinical trial, and some of them have been approved for clinical use and achieved excellent therapeutic effect. i.e. BCR-ABL inhibitor Gleevec for treating Philadelphia chromosome positive chronic myeloid leukemia and gastrointestinal stromal tumor; EGFR inhibitor Iressa and Tarceva for treating non-small-cell carcinoma etc. Gleevec is the first tumor drug with significant effect which was designed after knowing the pathogenesis of cancer. This drug is a milestone in molecular targeted cancer therapy. The greatness of Gleevec has been incorporated as one of the top ten science and technology news by SCIENCE magazine of USA in 2001.

Great success of the approved protein tyrosine kinase inhibitors further validates protein tyrosine kinases as promising molecular targets for clinic cancer therapy, and meanwhile validates its importance in tumor developing. Collective evidences show that protein tyrosine kinases encoded by mutant genes has direct relationship with the occurrence of tumor, such as BCR-ABL with chronic myeloid leukemia, c-Kit with GIST, SCCL and systemic mastocytosis, PDGFR with chronic myelomonocytic leukemia, dermatofibrosarcoma protuberan and hypereosinophilic syndrome, Flt3 with parts of acute granulocytic leukemia, B-Raf with melanoma, RET with thyroid carcinoma. In addition, c-KIT is also closely related to small cell lung cancer.

The first targeted therapy drug STI571 (Gleevec, Imatinib mesylate, Chinese name "Geliewei", Novartis Pharmaceuticals), a protein tyrosine kinase inhibitor, was approved by USA FDA in 2001 for treating chronic granulocytic leukemia (CML). This drug mainly targets Bcr-Abl, cKit, PDGFR etc. In clinic, single drug treatment with STI571 can make 98% of CML patients get relieved in clinical hematology, and 53% of these get relieved in cytogenetics.

However, emerging acquired resistance has become a major challenge for clinical management of CML With the widely application of STI571 in clinic, drug resistance has become a serious problem: part of cancer patients show primary resistance to STI571; some patients show effect at beginning of administration, but gradually show secondary resistance in the process of drug therapy. Resistance means after STI571 treatment, chronic-phase patients do not have complete hematologic response or patients at blast-phase and accelerated phase cannot recover back to chronic phase. In clinic, CML patients in blast-phase and ALL patients with positive BCR-ABL more generally develop resistance. About 70% of the two kinds of patients will develop STI571 resistance after 3~6 month drug administration. And once the resistance happens, the situation gets worse. Resistance is considered one defense by tumor cells to avoid being killed, and has many mechanisms which include: ① target gene (BCR-ABL, c-KIT, PDGFR) amplification; ② target gene mutation; ③ formation of the tumor clone independent of the target genes; ④ Production of α-1 acidic glycoprotein and over-expression of multiple drug resistance gene MDR1. However, the major mechanism publically accepted is secondary mutation in the kinase domains of kinase (BCR-ABL, c-KIT, PDGFR). Studies have demonstrated that that the common point mutations closely related to resistance include E255K, E255V, T315I and D276G of BCR-ABL, and D816V of c-KIT, etc. Patients with these mutations can easily have recurrence with bad prognosis. Some reports show that only 50% of patients of metastatic gastrointestinal stromal tumor (GIST), who carry V560G mutation in c-KIT transmembrane domain, respond to STI571 and achieve good efficacy. However, another 50% of patients of metastatic gastrointestinal stromal tumor do not respond to STI571. Point mutation of c-KIT tyrosine kinase (for example D816V, T315I) shows super resistance to STI571. In vitro experiments show that STI571 cannot inhibit proliferation of cells carrying c-KIT D816V and T315I mutants; patients of systemic mastocytosis carrying D816V c-KIT do not respond to STI571.

How to overcome the resistance of STI571 is a major important topic of today's Oncological medical study. Development of new small molecule inhibitors of tyrosine kinase is an important approach to overcome the resistance of STI571. For example, small molecule tyrosine kinase inhibitors, Nilotinib (AMN107), Dasatinib (BMS-354825) which launched to market recently, show effect on part (not all) of patient carrying STI571-resistant BCR-ABL point mutations (exclude T315 mutation). Same as that STI571 does, AMN107 competitively binds to non-active type of Abl kinase. It shows stronger affinity than STI571, and is 10~50 times more patent than STI571. AMN107 displays significant inhibition on cells harboring 15 point mutation except T315I with $IC_{50}$ values in 10~1000 nM. Different from STI571 and AMN107, BMS-354825 can bind and inhibit both the non-activated and the activated BCR-ABL. BMS-354825 displays significant inhibition on cells harboring 15 point mutation except T315I, with $IC_{50}$ values ranging from 10 nM to 125 nM. However, neither AMN107 nor BMS-354825 have effect on BCR-ABL T315I mutant. AMN107 and STI571 have no effect cells have c-KIT D816V point mutation. Therefore, it is urgently needed to develop new small molecule compounds which can efficiently kill the cells with STI571-resistant c-KIT point mutation (D816V) and/or BCR-ABL point mutation (including T315I) for both academia and industry of cancer therapy in the world.

In fact, most of today's protein tyrosine kinase inhibitor antitumor drugs can induce resistance related gene mutation, and face the problems of narrow clinic application scope. Therefore, development of the second generation of protein tyrosine kinase inhibitor and improvement of the clinic effect are super meaningful.

This invention relates to compounds with formula (I). These compounds can effectively inhibit different kinds of tumor cells, and display inhibitory potency targeting Gleevec-resistant mutants both in vitro and in vivo. These inhibitors represent a new generation of protein tyrosine kinase inhibitors.

SUMMARY OF THE INVENTION

It is an object of the present invention to provide a new type of heterocyclic alkynyl benzene compounds.

The technical solutions for solving the problem mentioned above are as followings:

compounds having formula (I) and their pharmaceutical acceptable salts, prodrugs, or stereoisomers:

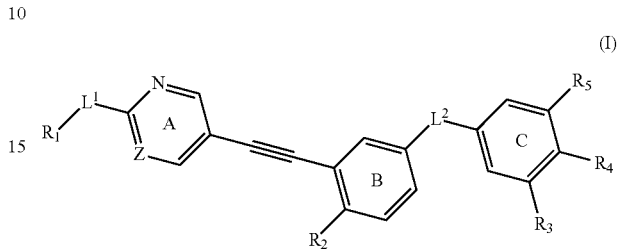

wherein Z is independently selected as CH or N;
$L^1$ is independently selected from NH, —N=, CH;
$L^2$ is independently selected as —CONH— or —NHCO—;
$R_1$ is independently selected from:
1. H;
2. $C_1$~$C_6$ alkyl;
3. $C_3$~$C_6$ cycloalkyl;
4. $C_1$~$C_5$ alkyl substituted by one or two hydroxyl group(s);
5. Phenyl;
6. Groups which can fuse A ring through $L^1$ in Z atom site to form fused penta-heterocycles containing 1~3 N atoms like

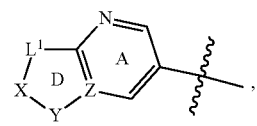

wherein, $L^1$ was defined as above; X, Y, Z are independently selected as N, CH; ring D is an aromatic heterocycle containing 1~3 N atoms;
$R_2$ is independently selected from
1. H;
2. Halogen (F, Cl, Br);
3. $C_1$~$C_5$ alkyl;
4. $C_3$~$C_6$ cycloalkyl;
5. $C_1$~$C_5$ alkyl containing F;
$R_3$ is independently selected from
1. H;
2. Halogen (F, Cl, Br);
3. $C_1$~$C_4$ alkyl;
4. $C_3$~$C_6$ cycloalkyl;
5. $C_1$~$C_4$ alkyl containing F;
when $R_5$ is H, $R_4$ is independently selected from
1. H;
2. $(CH_2)_n NR_6 R_7$;
3. $(CH_2)_n$-$Het^1$;
Or, when $R_4$ is H, $R_5$ is independently selected from
1. H;
2. $Het^2$;
n is independently selected from 0 or 1;
$Het^1$ is defined as nonaromatic heterocycle containing 1~3 N atoms; $Het^2$ is defined as aromatic five-member heterocycle containing 1~3 hetero atoms like N, O, S; alkyl, cycloalkyl or $NR_6R_7$ will be incorporated into any C or N position in $Het^1$ and $Het^2$ which can be substituted;

$R_6$ or $R_7$ is independently selected from:
1. H;
2. $C_1$~$C_3$ alkyl;
3. $C_1$~$C_3$ alkyl containing F;
4. $C_3$~$C_6$ cycloalkyl;

$R_6$ and $R_7$ can further form penta-, hexa-, hepta- or oct-atomic ring structure through C, O, N, S atoms.

Preferably, Z is N, $L^1$ is NH, $R^1$ is preferably selected from:
1. methyl, ethyl, isopropyl, tert-butyl;
2. cyclopropyl, cyclobutyl, cyclopentyl, cyclohexyl;

Preferably $R_1$ and A form fused ring through as

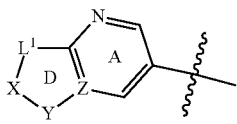

which is preferably selected from

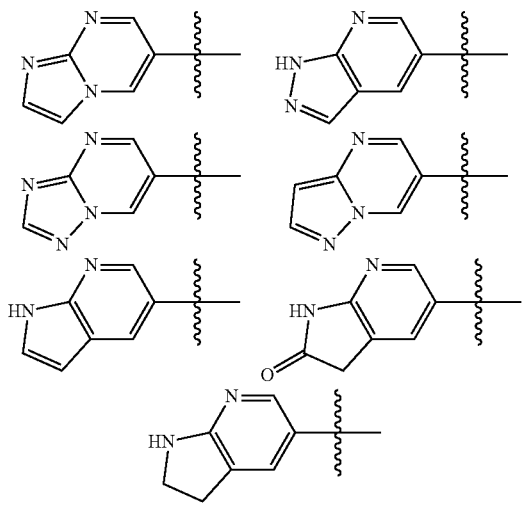

$R_2$ is selected from:
1. H
2. methyl, ethyl, isopropyl, tert-butyl;
3. cyclopropyl;
4. F, Cl, Br;
5. $CF_3$ Preferably C ring is selected from:

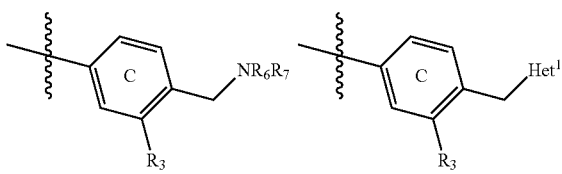

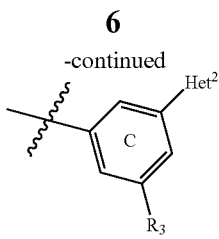

$R_3$, $R_6$, $R_7$ have the same definition as above mentioned; $Het^1$ has the same definition as above mentioned, $Het^2$ is selected from substituted imidazole, substituted pyrazole, substituted oxazole, substituted triazole, substituted oxazolidine, substituted thiazole.

Preferably, in another embodiment, compound having formula (I) and their pharmaceutical acceptable salts, prodrugs, or stereoisomers is more preferably selected from:

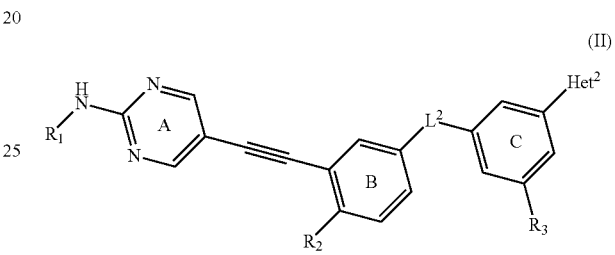
(II)

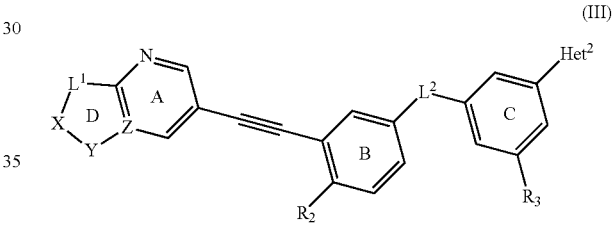
(III)

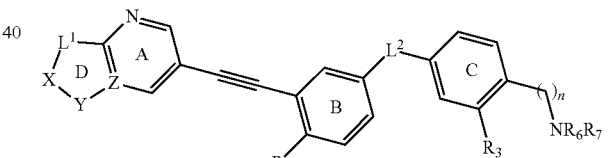
(IV)

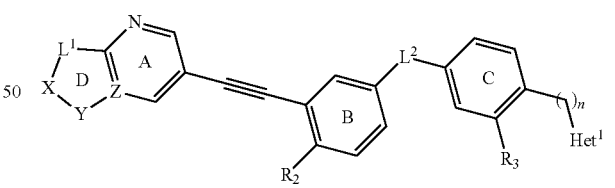
(V)

wherein

X, Y, Z are independently selected from N, CH; D heterocycle contains 1~3 N atoms; the fused ring of D with A ring is selected from:

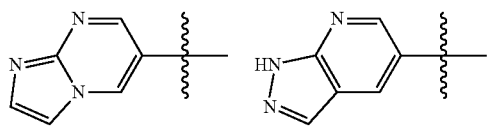

-continued

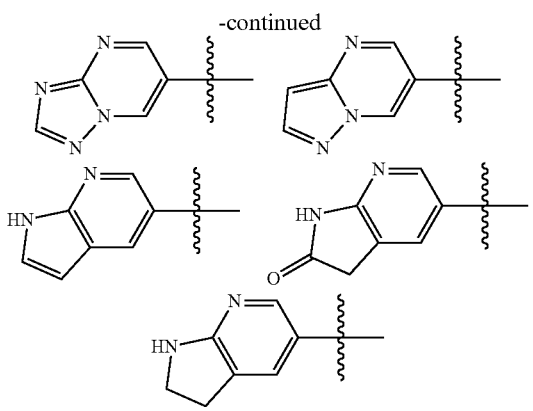

$R_1$, $R_2$, $R_3$, $R_6$, $R_7$, n, L', $L^2$, $Het^1$, $Het^2$ have the same definition as above mentioned.

It is a further object for the present invention to provide the application of above mentioned compounds.

The compounds mentioned above or their pharmaceutically acceptable salts, stereoisomers or pro-drugs thereof can be used as new therapeutic agents for the treatment or the prevention of cancer.

The invention also relates to that the above mentioned compounds in effective dose can be used for the treatment of over-proliferative diseases, such as gastrointestinal stromal tumors (GIST), histiocytic lymphoma, non-small cell lung cancer, small cell lung cancer, lung adenocarcinoma, squamous cell lung carcinoma, pancreatic cancer, breast cancer, prostate cancer, liver cancer, skin cancer, squamous cell carcinoma, nasopharyngeal carcinoma, leukemia, and so on.

The compounds mentioned above and their pharmaceutical acceptable salts of the present invention can inhibit the proliferation of numerous cancers effectively, and inhibit protein kinases including BCR-ABL, c-Kit, PDGF, and can be used as anti-tumor drugs, and overcome the clinically induced resistance against Gleevec. As can be understood by the technical person in the field, the compounds and their pharmaceutical acceptable salts of the present invention can be used for the therapeutic application of over proliferative diseases including human cancers or mammalian cancers.

DETAILED DESCRIPTION OF THE PREFERRED EMBODIMENTS

Figure 1:
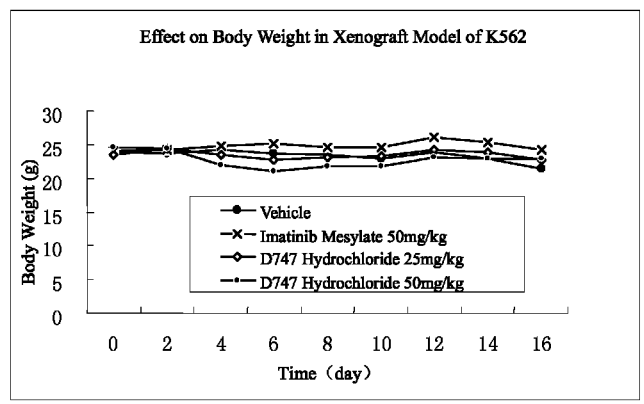
FIG. 1 is the schematic diagram of effect of compound D747 Hydrochloride (po,qd) on body weight in Xenograft model of K562 in Example 1.

In the compounds mentioned in the present invention, when any variables (such as R1, R, etc.) appear more than once in any component, the definitions every time they occur are independent from the definitions they appear other times. Also, allow substituent and variable combination, as long as the combination makes stable compounds. The line crossing from the substituent to ring system means the bond indicated can link to any atom of the ring which can be substituted. If the ring system is multiple ring system, it means the bond only connects to any appropriate carbon atom of the adjacent ring. The person with common techniques in the art can choose the compounds substituent and replacement type in order to provide the synthetic compounds that are chemically stable and can be synthesized from easily available materials by the techniques in the field and the methods mentioned below. If the substituent itself is replaced by more than one group, these groups can be in the same carbon atom or different carbon atoms, as long as the structure is stable.

In this invention, the term "alkyl" and "sub-alkyl" means a branched-chain or straight chain alkyl group with the certain number of carbon atoms. For example, the definition of "$C_1$-$C_5$" in "$C_1$-$C_5$ alkyl" means straight-chain or branched-chain alkyl group with 1, 2, 3, 4 or 5 carbon atoms. For example, "$C_1$-$C_5$ alkyl" includes methyl, ethyl, n-propyl, isopropyl, n-butyl, tert-butyl, isobutyl, pentyl, etc. The term "cycloalkyl" refers to a specific single saturated ring alkyl with the certain number of carbon atoms. For examples, "cycloalkyl" includes cyclopropyl-, methyl-cyclopropyl-, 2,2-dimethyl-cyclobutyl, 2-ethyl-cyclopentyl-, cyclohexyl etc.

In this invention, the term of "hetero aryl group" is a stable monocyclic ring with up to six atoms or a stable bicyclic ring in which each ring contains up to six atoms. At least one of the rings is an aromatic ring containing 1~4 atoms selected from O, N or S. Hetero aryl groups include but not limit to: imidazolyl, triazolyl, pyrazolyl, furanyl, thienyl, oxazolyl, isoxazolyl, pyrazinyl, pyridazinyl, pyridyl, pyrimidinyl, pyrrolyl. About the definition of hetero aryl, any hetero aryl N-oxidation derivatives containing N atom should also be added. When hetero aryl substituted group is a bicyclic ring and one of the two rings is non-aromatic or non-hetero-atom containing ring, this bicyclic ring is fused through the aromatic ring or hetero atoms.

The term of "Heterocycle" refers to an aromatic or nonaromatic ring containing 5~6 atoms, in which contains 1~4 hetero atoms such as O, N, S. "Heterocycle" includes hetero aromatic ring as mentioned above; it also includes dihydro and tetrahydro analogs. "Heterocycles" further include but not limit to: imidazolyl, indolyl, isothiazolyl, isoxazolyl, oxadiazolyl, oxazolyl, oxetanyl, pyranyl, pyrazinyl, pyrazolyl, pyridazinyl, pyridyl, pyrimidinyl, pyrrolyl, quinazolinyl, tetrazolyl, thiadiazolyl, thiazolyl, thienyl, triazolyl, 1,4-alkyl-dioxinyl, alkyl pyrrolidinyl, dihydro-imidazolyl, dihydro-isoxazolyl, dihydro-iso thiazolyl, dihydro-oxadiazolyl, dihydro-oxazolyl, dihydro-pyrazinyl, dihydro-pyrazolyl, dihydro-pyridyl, dihydro-pyrimidinyl, dihydro-pyrrolyl, dihydro-tetrazolyl, dihydro-thiadiazolyl, dihydro-thiazolyl, dihydro-thienyl, dihydro-triazolyl, methylene dioxy-benzophenone acyl, tetrahydrofuranyl, tetrahydrothiopheneyl, and their N-oxides etc. The linkage of heterocycle substituent can be achieved through C atom or heteroatom. In one embodiment, heterocycle is selected from imidazolyl, pyridyl, 1-pyrrolidone, 2-piperidone, 2-pyrimidone, 2-pyrrolidone, thienyl, oxazolyl, triazolyl, isoxazolyl, etc.

As understood by the person skilled in the prior art, "halo" or "halogen" in the present specification means chlorine, fluorine, bromine and iodine.

Unless specially mentioned, alkyl, cycloalkyl, aryl, hetero aryl, heterocyclic groups can be substituted or not be substituted. For example, $C_1$-$C_6$ alkyl group can be substituted by one, two, or three substituents selected from OH, halogens, alkoxyl, dialkylamino, or heterocyclic ring such as morpholinyl, piperidinyl groups.

In an embodiment, Het may form a single ring containing 4~7 atoms or a bicyclic ring in which each ring comprises 4~7 atoms through the N atom which connects the Het, the single ring or bicyclic ring may further comprises 1~2 hetero atoms selected from N, O, S, and said heterocyclecan also be substituted by one or more substituents selected from $R_2$. The hetero cyclic rings formed include but not limit to the following heterocycles, and it shall be remembered said heterocycle selectively substituted by one or more (preferably one, two or three) substituents selected from $R_2$.

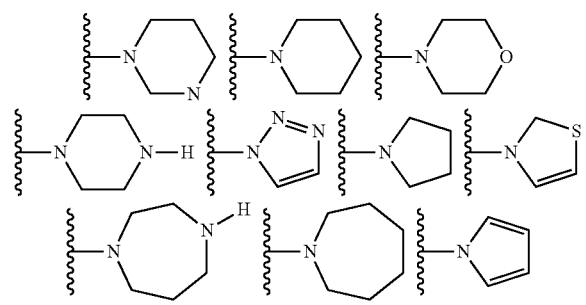

-continued

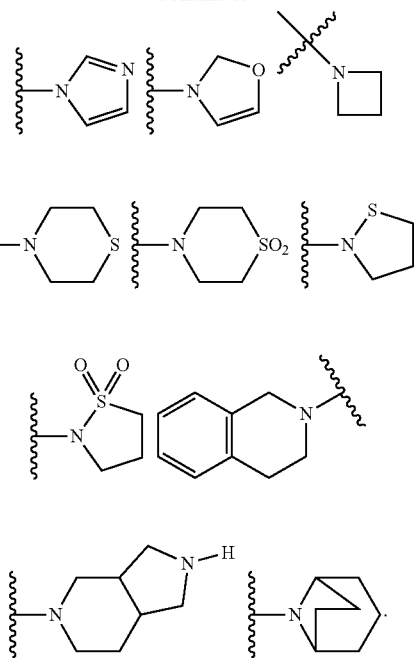

The invention relates to the free forms of compounds with formula (I)~(II), and it also relates to their pharmaceutical acceptable salts or steroisomers. The specific examples in the invention are the protonated salts of amines.

Therefore, "pharmaceutical acceptable salts" in the invention mean the normal nontoxic salts formed by the basic compounds in the invention with organic acids and inorganic acids. For example, the normal nontoxic salts are from inorganic acids that include hydrochloric acid, hydrobromic acid, sulfuric acid, sulfamic acid, phosphoric acid, nitric acid, and from organic acids that include acetic acid, propionic acid, succinic acid, glycolic acid, stearic acid, lactic acid, malic acid, tartaric acid, lemon acid, ascorbic acid, bashing acid, maleic acid, hydroxy-maleic acid, phenylacetic acid, glutamic acid, benzoic acid, salicylic acid, sulfanilic acid, 2-acetoxy-benzoic acid, p-toluenesulfonic acid, methanesulfonic acid, ethane disulfonic, oxalic acid, hydroxyethyl sulfonic acid, trifluoroacetic acid etc.

Berg et al described the preparation of pharmaceutical acceptable salts as above mentioned or other typical pharmaceutical acceptable salts in Pharmaceutical Salts, *J. Pharm. Sci.* 1977, 66: 1-19 in more details.

The compounds of the present invention can be prepared by using the following method besides the method which is well validated in the experimental procedures or has been published in articles. Therefore the synthetic scheme below only outlines the examples and does not limit the compounds or any specific substituent. The number of the substituents in the scheme does not need to comply with the number specified in the Claims. And for clear explanation, the formula (I) showing only single substitution can allow compounds with multiple substituents.

As shown in the scheme A, compounds in formula (I) was synthesized through five steps by using 3-bromo-5-(trifluoromethyl)benzenamine as the starting material.

Scheme A

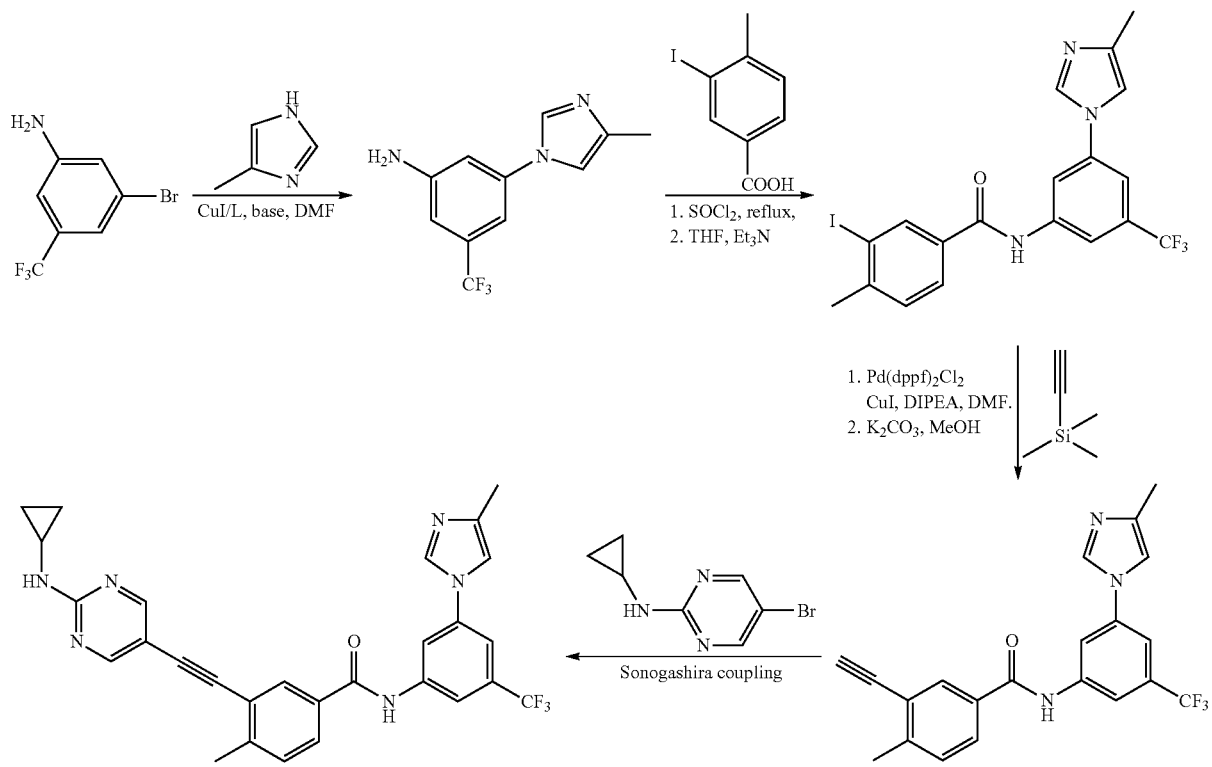

In one embodiment, this present invention provides a method of using compounds in formula (I) and their pharmaceutical acceptable salts for treatment of over proliferative diseases including human cancers or mammalian cancers.

In one embodiment, the invention also relates to the compounds designed in the present invention and their pharmaceutically acceptable salts which are used for the treatment or the prevention of over proliferative diseases, such as gastrointestinal stromal tumors (GIST), histiocytic lymphoma, non-small cell lung cancer, small cell lung cancer, lung adenocarcinoma, squamous cell lung carcinoma, pancreatic cancer, breast cancer, prostate cancer, liver cancer, skin cancer, squamous cell carcinoma, nasopharyngeal carcinoma, leukemia, and so on.

In one embodiment, the compounds designed in the present invention and their pharmaceutically acceptable salts can be used in combination with other modulators in clinic or under investigation to strengthen their clinical potency, such as estrogen receptor modulator, androgen receptor modulator, retinoid receptor modulator, cell toxin/cell inhibitor, antiproliferative agent, protein transferase inhibitor, HMG-CoA reductase inhibitor, HIV protein kinase inhibitor, reverse transcriptase inhibitor, angiogenesis inhibitor, cell proliferation and survival signaling inhibitor, interference with the cell cycle checkpoint drug and apoptosis inducing agent, cytotoxic drug, protein tyrosine inhibitor, EGFR, VEGFR inhibitor, serine/threonine protein inhibitor, Bcr-Abl inhibitor, c-Kit inhibitor, Met inhibitor, Raf inhibitor, MEK inhibitor, MMP inhibitor, topoisomerase inhibitor, histidine deacetylase inhibitor, proteasome inhibitor, CDK inhibitor, Bcl-2 family protein inhibitor, MDM2 family protein inhibitor, inhibitors of IAP family proteins, inhibitors of STAT family proteins, PI3K inhibitor, AKT inhibitor, integrin blockade inhibitor, IFN-α, interleukin-12, COX-2 inhibitors, p53, p53 activators, VEGF antibody, EGF antibody, etc.

The compounds of the present invention and their pharmaceutically acceptable salts can be used to treat the following diseases according to the following methods, as well as other diseases not listed below:

(1)
A method for treating breast cancer in a human or other mammalian patient in need of such treatment which comprises administering to the patient a pharmaceutical composition comprising a compound of Formula (I) in present invention and its pharmaceutically acceptable salt. The breast cancers include but are not limited to invasive ductal carcinoma, invasive lobular carcinoma, ductal carcinoma in situ and lobular carcinoma in situ.

(2)
A method for treating respiratory tract cancer in a human or other mammalian patient in need of such treatment which comprises administering to the patient a pharmaceutical composition comprising a compound of Formula (I) in present invention and its pharmaceutically acceptable salt. The respiratory tract cancer includes but not limited to small-cell lung cancer, non-small cell lung cancer, bronchial adenoma and pleuropulmonary blastoma.

(3)
A method for treating brain cancer in a human or other mammalian patient in need of such treatment which comprises administering to the patient a pharmaceutical composition comprising compound of Formula (I) in the present invention and its pharmaceutically acceptable salt. The brain cancers includes but not limited to brainstem and subocular glioma, the cerebellum and cerebral astrocytoma, ependymal cell tumor, neuroectodermal and pineal tumor.

(4)
A method for treating cancers in the male/female reproductive organism in a human or other mammalian patient in need of such treatment which comprises administering to the patient a pharmaceutical composition comprising a compound of Formula (I) in the present invention and its pharmaceutically acceptable salt. Cancers in the male reproductive organism include but are not limited to prostate cancer and testicular cancer. Cancers in the female reproductive organism include but not limit to endometrial cancer, cervical cancer, ovarian cancer, cancer of the vagina and vulva and uterine tumor;

(5) A method for treating cancers in the alimentary canals in a human or other mammalian patient in need of such treatment which comprises administering to the patient a pharmaceutical composition comprising a compound of Formula (I) in the present invention and its pharmaceutically acceptable salt. Cancers in the alimentary canals include but are not limited to anal cancer, colon cancer, colon cancer, esophageal cancer straight, gastric cancer, pancreatic cancer, small bowel or salivary gland cancer;

(6) A method for treating cancers in the urethra in a human or other mammalian patient in need of such treatment which comprises administering to the patient a pharmaceutical composition comprising a compound of Formula (I) in the present invention and its pharmaceutically acceptable salt. Cancers in the urethra include but are not limited to bladder cancer, penile cancer, renal cell carcinoma, carcinoma of renal pelvis, ureter cancer or carcinoma of urethra;

(7) A method for treating cancers in the eyes in a human or other mammalian patient in need of such treatment which comprises administering to the patient a pharmaceutical composition comprising a compound of Formula (I) in the present invention and its pharmaceutically acceptable salt. Cancers in the eyes include but are not limited to intraocular melanoma and retinoblastoma;

(8) A method for treating cancers in the liver in a human or other mammalian patient in need of such treatment which comprises administering to the patient a pharmaceutical composition comprising a compound of Formula (I) in the present invention and its pharmaceutically acceptable salt. Cancers in the liver include but are not limited to liver cell tumor (with or without fiber board variations of stem cell carcinoma), bile duct carcinoma (Intrahepatic bile duct carcinoma) and mixed hepatocellular carcinoma of bile duct;

(9) A method for treating cancers in the skin in a human or other mammalian patient in need of such treatment which comprises administering to the patient a pharmaceutical composition comprising a compound of Formula (I) in the present invention and its pharmaceutically acceptable salt. Cancers in the skin include but are not limited to squamous cell carcinomas, Kaposi's sarcoma, malignant melanoma, Merck's cells in skin cancer and melanoma cells cancer;

(10) A method for treating cancers in the head and neck in a human or other mammalian patient in need of such treatment which comprises administering to the patient a pharmaceutical composition comprising a compound of Formula (I) in the present invention and its pharmaceutically acceptable salt. Cancers in the head and neck include but are not limited to the larynx, hypopharynx, nasopharynx, oropharynx cancer and cancer of the mouth and lips;

(11) A method for treating lymphoma cancers in a human or other mammalian patient in need of such treatment which comprises administering to the patient a pharmaceutical composition comprising a compound of Formula (I) in the present invention and its pharmaceutically acceptable salt. Lymphoma cancers include but are not limited to AIDS related lymphoma, non-Hodgkin lymphoma, cutaneous T cell lymphoma, Hodgkin's disease and central nervous system lymphoma;

(12) A method for treating sarcoma cancers in a human or other mammalian patient in need of such treatment which comprises administering to the patient a pharmaceutical composition comprising a compound of Formula (I) in the present invention and its pharmaceutically acceptable salt. Cancers in the eyes include but are not limited to soft tissue sarcomas, osteosarcoma, malignant fibrous histiocytoma, lymphatic sarcoma and rhabdomyosarcoma;

(13) A method for treating leukemia in a human or other mammalian patient in need of such treatment which comprises administering to the patient a pharmaceutical composition comprising a compound of Formula (I) in the present invention and its pharmaceutically acceptable salt. Leukemia include but are not limited to acute myeloid leukemia, acute leukemia, chronic lymphocytic leukemia and forest cell leukemia, chronic myelogenous leukemia and hairy cell leukemia;

Administration and Dose Ranges

Based on the standard pharmaceutical technology, the compound of the present invention can be used alone or in the pharmaceutical combination with pharmaceutical acceptable acceptors, accessories or diluents to a mammal, preferably a human. For example, oral, rectal, topical, parenteral, ocular, pulmonary, nasal, and intestines and stomach may be employed.

In one embodiment, when treating or controlling cancer of the patient with which compounds of Formula (I) are used, oral daily dosage of the compounds of the present invention administered is from about 0.1~500 mg/day/kg body weight. The proper administration is as a single daily dose or as divided doses two to four times a day, or in sustained release form. For most large mammals, the total daily dosage is from about 0.1~1500 mg/day/kg body weight, preferably from about 0.5~100 milligrams/day/kg body weight. In the case of a 70 kg adult human, the total daily dose will generally be 0.5~100 mg/day/kg body weight. In the case of a 70 kg adult human, the total daily dose will generally be from about 1 milligram to about 500 milligrams. For a particularly potent compound, the dosage for an adult human may be as low as 0.1 mg/day.

Metabolites-Prodrugs

The metabolites of the compounds and their pharmaceutical salts in the present invention, and prodrugs that are converted to the compounds and their pharmaceutical salts in the present invention are comprised in the claims of the present application.

Combination Therapy

Compounds of Formula I~II may be used in combination with other drugs that are known to be useful in the treatment or amelioration of the diseases or similar diseases. In the combination administration, such other drugs may be administered, by a route administration and in an amount commonly used, and contemporaneously or sequentially with a compound of Formula I~II. When a compound of Formula I~II is used contemporaneously with one or more other drugs, a pharmaceutical composition containing one or more other known drugs and the compound of Formula I~II is preferred. The combination therapy also comprises therapies in which the compound of Formula I~II and one or more other known drugs are administered on overlapping schedules. When used in combination with one or more other drugs, the compound of Formula I~II and the other known drugs may be used in lower dosage than when they are used alone. Drugs or active ingredients used in combination with compounds of Formula I~II comprises but are not limited to: estrogen receptor modulator, androgen receptor modulator, retinoid receptor modulator, cell toxin/cell inhibitor, antiproliferative agents, protein transferase inhibitors, HMG-CoA reductase inhibitors, HIV protein kinase inhibitors, reverse transcriptase inhibitors, angiogenesis inhibitors, cell proliferation and survival signaling inhibitors, interference with the cell cycle checkpoint drugs and apoptosis inducing agent, cytotoxic drugs, protein tyrosine inhibitor, EGFR, VEGFR inhibitors, inhibitors of serine/threonine protein inhibitors, inhibitors of Bcr-Abl, c-Kit inhibitor, Met inhibitors, inhibitors of Raf, MEK inhibitor, MMP inhibitors, inhibitors of topoisomerase, histidine deacetylase inhibitors, proteasome inhibitors, inhibitors of CDK, Bcl-2 family protein inhibitor, MDM2 family protein inhibitors, inhibitors of IAP family proteins, inhibitor of STAT family proteins, PI3K, AKT inhibitors, inhibitors of integrin blockade, IFN-α, interleukin-12, COX-2 inhibitor, p53, p53 activator inhibitor, VEGF antibody, EGF antibody, etc.

In one embodiment, drugs or active ingredients used in combination with compounds of Formula I~II comprises but are not limited to: Aldesleukin, Alendronate, interferon, Alitretinoin, allopurinol, allopurinol sodium, palonosetron hydrochloride, Hemel, amino glutethimide, amifostine, amrubicin, Ann acridine, anastrozole, dolasetron, Aranesp, arglabin, arsenic trioxide, Aromasin, 5N cytidine, azathioprine, BCG or BCG, Bestatin hydrochloride, betamethasone acetate, betamethasone sodium phosphate, Bexarotene, bleomycin sulfate, broxuridine, bortezomib, busulfan, calcitonin, Alemtuzumab Campath, capecitabine, carboplatin, Casodex, cefesone, Seamus IL, DNR, chlorambucil, cisplatin, cladribine, cladribine, chloride phosphoric acid, Cytarabine, cyclophosphamide, Dacarbazine, Actinomycin D, DNX, dexamethasone, dexamethasone phosphate, estradiol valerate, cefdinir interleukin 2, Methylprednisolone acetate, deslorelin, dexrazoxane, diethylstilbestrol, Diflucan, docetaxel, doxorubicin, doxifluridine, dronabinol, chin-166-chitosan complexes, eligard, rasburicase, epirubicin hydrochloride, aprepitant, epirubicin, alfa-epoetin, erythropoietin, Eptaplatin, levamisole, estradiol formulation, 17-β-estradiol, estramustine phosphate sodium, ethinylestradiol, Amifostine, hydroxyl phosphate, Etopophos, etoposide, Fadrozole, tamoxifen, filgrastim, finasteride, floxuridine, fluconazole, fludarabine, 5-fluorine BrdU a phosphate, 5-fluorouracil, fluoxymesterone, flutamide, formestane, Cytarabine hydrochloride, Fotemustine, fulvestrant, immunoglobulin, gemcitabine, gemtuzumab ozogamicin, imatinib mesylate, carmustine capsules, goserelin, hydrocortisone, erythro-hydroxy nonyl adenine, hydroxyurea, Ibritumomab Tiuxetan. Idarubicin, ifosfamide, interferon α, IFN-α2, interferon α-2A, interferon α-2B, interferon α-nl, IFN α-n3, interferon β, interferon γ-la, IL-2, intron A, Iressa, Irinotecan, Kytril, mushroom polysaccharide sulfate, letrozole, leucovorin, leuprolide, leuprorelin acetate, Levamisole, levorotation folinic acid calcium salt, levothyroxine sodium, levothyroxine sodium, lomustine, lonidamine, dronabinol, nitrogen mustard, Mecobalamin, medroxyprogesterone acetate, megestrol acetate, melphalan, esterified estrogens, 6-Mercaptopurine, mesna, methotrexate, aminolevulinic acid methyl ester, miltefosine, minocycline, mitomycin C, mitotane, mitoxantrone anthraquinone, Trilostane, citric acid adriamycin liposome, Nedaplatin, Pegfilgrastim, oprelvekin, neupogen, nilutamide, tamoxifen, NSC-631570, recombinant human interleukin 1-β, octreotide, Ondansetron hydrochloride, hydroprednisone oral solution, oxaliplatin, paclitaxel, prednisone, L-asparaginase enzyme sodium phosphate preparation, Pegasys, pentostatin, Picibanil, pilocarpine hydrochloride, adjoin THP, mithramycin, porfimer sodium, prednimustine, Prednisolone Steaglate, prednisolone, Premarin, C kappa umbilical, recombinant human erythropoietin, raltitrexed, Libby, etidronate rhenium-186, rituximab, Redoxon-A, Romo peptide, pilocarpine hydrochloride tablets, octreotide, Sargramostim, semustine, Schizophyllan, sobuzoxane, Methylprednisolone, Paphos acid, stem cell therapy, streptozocin, strontium chloride-89, levothyroxine sodium, tamoxifen, tamsulosin, TNF-alfa, tastolactone, docetaxel, teceleukin, temozolomide, teniposide, propionic acid testosterone, testosterone propionate, thioguanine, thiotepa, thyroid stimulating hormone, Tiludronic acid, topotecan, toremifene, tositumomab, trastuzumab, Treosulfan, Victoria A acid, methotrexate tablets, three methyl melamine, trimetrexate, triptorelin, double hydroxy acetic acid Naphthalene of triptorelin, UFT, uridine, valrubicin, vesnarinone, alkali, vincristine, Vindesine Vinorelbine, virulizin, dextral razoxane, Zinostatin ester, ondansetron, paclitaxel, acolbifene, Interferon r-lb, affinitak, aminopterin, Arzoxifene, Asoprisnil, atamestane, atrasentan, BAY 43-9006, Avastin, CCI-779, CDC-501, Celebrex, cetuximab, crisnatol, cyproterone acetate, decitabine, DN-101, Doxorubicin-MTC, dSLIM, dutasteride, edotecarin, eflornithine, Exatecan, Fenretinide, histamine hydrochloride, holmium-166 DOTMP, ibandronate, IFN-γ, intron-PEG, ixabepilone, intron keyhole shaped hemocyanin, L-651582, Lanreotide, lasofoxifene, Libra, lonafamib, Miproxifene, MS-209, liposome MTP-PE, MX-6, Nafarelin, Nemorubicin, Neovastat, Nolatrexed, Aolimosen, onco-TCS, osidem, paclitaxel poly glutamic acid ester, pamidronate disodium injection, PN-401, QS-21, R-1549, raloxifene, ranpirnase, 13-cis-Victoria A acid, satraplatin, seocalcitol, T-138067, Tarceva, DHA-PTX, thymosin al, Pirazofurin, tipifarnib, tirapazamine, TLK-286, toremifene, trans MID-lo7R, valspodar, vapreotide, vatalanib, verteporfin, Vinflunine, Z-100 and Zoledronic acid or their combination.

Further explanations are made as followings, but those embodiments cannot be used to limit the protection scope of the invention.

Example 1

3-(2-(2-(cyclopropylamino)pyrimidin-5-yl)ethynyl)-4-methyl-N-(3-(4-methyl-1H-imidazol-1-yl)-5-(trifluoromethyl)phenyl)benzamide

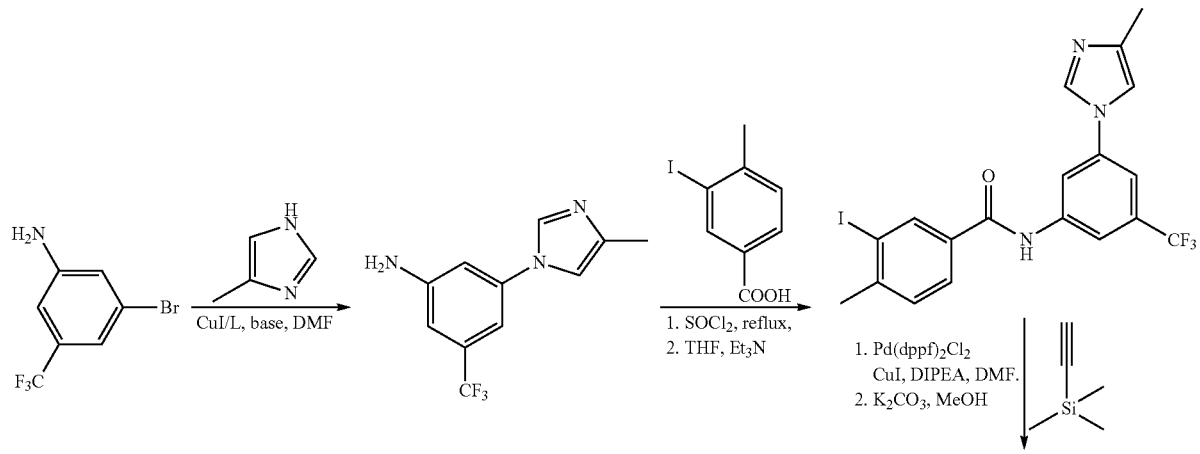

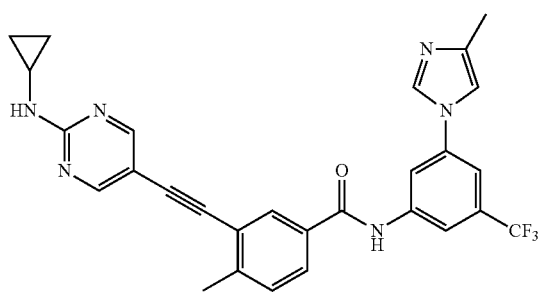
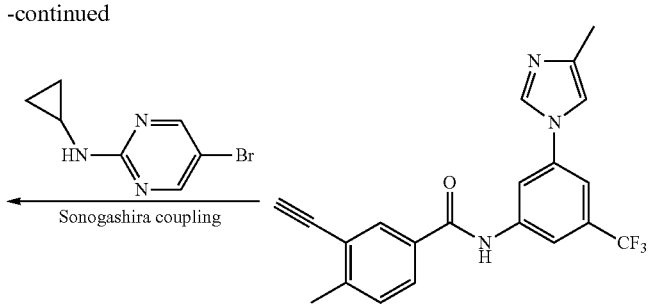

Sonogashira coupling

-continued

Step 1. 5-(4-methyl-1H-imidazol-1-yl)-3-(trifluoromethyl)-benzenamine

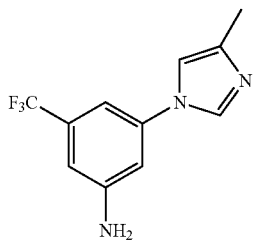 [SMILES: Cc1cn(-c2cc(N)cc(C(F)(F)F)c2)cn1]

In a pressure tube with one end sealed, add 190 mg CuI (1 mmol), 1.64 g 4-methyl-1H-imidazole (20 mmol), 3.25 g Cs₂CO₃ (10 mmol), and after Nitrogen replacement, add 2.40 g 3-bromo-5-(trifluoromethyl)aniline (10 mmol), 350 mg 1-(5,6,7,8-tetrahydroquinolin-8-yl)ethanone (2 mmol) and 30 mL DMF was added into a flask. The mixture was stirred at 110° C. for 18 h under sealing. After cooling to room temperature, the solvent was removed under vacuum and the residue was purified by column chromatography to afford 2.19 g desired product (91%).
¹H NMR (400 MHz, d-DMSO), δ 8.06 (s, 1H), 7.35 (s, 1H), 6.97 (s, 1H), 6.93 (s, 1H), 6.81 (s, 1H), 5.87 (br, 2H), 2.15 (s, 3H). MS (ESI), m/z: 242 (M⁺+H⁺).

Step 2. 3-iodo-4-methyl-N-(3-(4-methyl-1H-imidazol-1-yl)-5-(trifluoromethyl)phenyl)benzamide

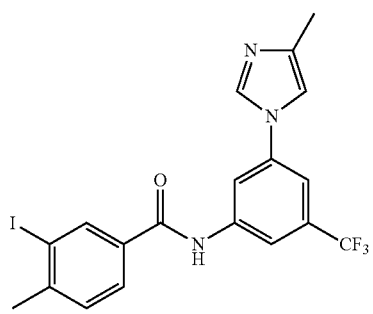 [SMILES: Cc1cn(-c2cc(NC(=O)c3ccc(C)c(I)c3)cc(C(F)(F)F)c2)cn1]

Add 2 drops of DMF into 628 mg 3-iodo-4-methylbenzoic acid (2.2 mmol) in 20 mL SOCl₂ and reflux for 2 h. After vacuum evaporation of SOCl₂, add 6.0 mL anhydrous THF and get the pale yellow solution. Dissolve the product from step 1, 524 mg 5-(4-methyl-1H-imidazol-1-yl)-3-(trifluoromethyl)-benzenamine (2.0 mmol) in 6.0 mL anhydrous THF and add 10 mmol Et₃N, and the pale yellow solution prepared previously is added drop wise till it is all added. The reaction mixture rises to room temperature for 1 hr. The reaction was quenched with addition of brine and extracted with EtOAc. The combined extraction organic layers was dried and concentrated under vacuum, the residue was purified through column chromatography to afford 873 mg desired product. (90%)

MS (ESI), m/z: 486 (M⁺+H⁺).

Step 3. 3-ethynyl-4-methyl-N-(3-(4-methyl-1H-imidazol-1-yl)-5-(trifluoromethyl) phenyl)benzamide

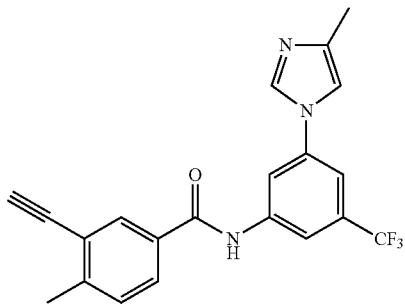 [SMILES: C#Cc1cc(C(=O)Nc2cc(-n3cnc(C)c3)cc(C(F)(F)F)c2)ccc1C]

In a pressure tube with one end sealed, add 485 mg 3-iodo-4-methyl-N-(3-(4-methyl-1H-imidazol-1-yl)-5-(trifluoromethyl)phenyl)benzamide (1.0 mmol) from Step 2, 500 mg trimethylsilylacetylene (5.0 mmol), 19 mg CuI (0.1 mmol), 7 mg Pd(PPh₃)₂Cl₂ (0.01 mmol), 1.0 mL Et₃N in 3.0 mL acetonitrile, and after Nitrogen replacement, the mixture is stirred at 80° C. for 2 h. After cooling to room temperature, the solution was filtered by 2 cm silica gel column. The filtration is washed three times with ethyl acetate and is concentrated to brown solid which is further dissolved in 5 mL methanol. The solution is then added with 980 mg K₂CO₃ and stirred at room temperature for 3 h. The solid was filtered off and the solution was concentrated to column chromatography f 344 mg desired product. (90%)

MS (ESI), m/z: 384 (M⁺+H⁺).

Step 4. 5-bromo-N-cyclopropylpyrimidin-2-amine

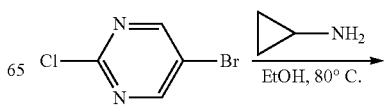

-continued

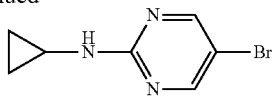

In a pressure tube with one end sealed, add 193 mg 5-bromo-2-chloropyrimidine (1.0 mmol) and 285 mg cyclopropylamine (5.0 mmol) in 3.0 mL ethanol, and the mixture is heated to 80° C. and stirred for 3 h. The reaction mixture was cooled to room temperature, and 203 mg solid product was collected by filtration for direct use yield: 95%).

MS (ESI), m/z: 215 (M$^+$+H$^+$).

Step 5. 3-(2-(2-(cyclopropylamino)pyrimidin-5-yl)ethynyl)-4-methyl-N-(3-(4-methyl-1H-imidazol-1-yl)-5-(trifluoromethyl)phenyl)benzamide (D747)

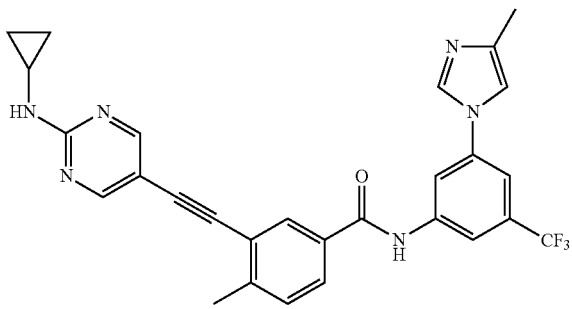 [SMILES: Cc1cn(-c2cc(NC(=O)c3ccc(C)c(C#Cc4cnc(NC5CC5)nc4)c3)cc(C(F)(F)F)c2)cn1]

In a pressure tube with one end sealed, add 192 mg step 3 product, 3-ethynyl-4-methyl-N-(3-(4-methyl-1H-imidazol-1-yl)-5-(trifluoromethyl)phenyl)benzamide (0.5 mmol), 107 mg Step 4 product, 5-bromo-N-cyclopropylpyrimidin-2-amine (0.5 mmol), 19 mg CuI (0.1 mmol), 2.2 mg Pd(OAc)$_2$ (0.01 mmol), 2.8 mg PCy$_3$ (0.01 mmol) 3.0 mL DMF, 193 mg DIPEA (1.5 mmol), after nitrogen replacement, the solution is heated to 60° C. for 12 h. After cooling to room temperature, the solid is filtered off by 2 cm silical gel column and washed by ethyl acetate for three times, and the solution was concentrated by vacuum evaporation for 193 mg desired product (75%).

$^1$HNMR (400 MHz, d-DMSO), δ ppm 10.69 (s, 1H), 8.54 (br, 2H), 8.29 (s, 1H), 8.21 (s, 1H), 8.16 (m, 2H), 7.93 (m, 2H), 7.73 (s, 1H), 7.52 (m, 2H), 2.77 (m, 1H), 2.53 (s, 3H), 2.18 (s, 3H), 0.71 (m, 2H), 0.53 (m, 2H). MS (ESI), m/z: 517 (M$^+$+H$^+$).

Example 2

N-(3-(1H-imidazol-1-yl)-5-(trifluoromethyl)phenyl)-3-(2-(2-(cyclopropylamino)pyrimidin-5-yl)ethynyl)-4-methylbenzamide (D729)

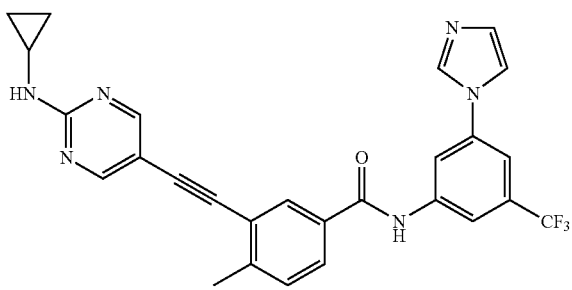 [SMILES: Cc1ccc(C(=O)Nc2cc(-n3ccnc3)cc(C(F)(F)F)c2)cc1C#Cc1cnc(NC2CC2)nc1]

The compound was synthesized by using the procedure similar to that of Example 1.

$^1$HNMR (400 MHz, d-DMSO), δ ppm 10.73 (s, 1H), 8.55 (br, 2H), 8.33 (d, J=2.4 Hz, 2H), 8.21 (s, 1H), 8.14 (d, J=1.2 Hz, 1H), 7.94-7.89 (m, 2H), 7.80-7.76 (m, 2H), 7.53 (d, J=8.4 Hz, 1H), 7.17 (s, 1H), 2.78-2.73 (m, 1H), 2.53 (s, 3H), 2.18 (s, 3H), 0.73-0.68 (m, 2H), 0.53-0.49 (m, 2H). MS (ESI), m/z: 503 (M$^+$+H$^+$).

Example 3

4-methyl-N-(3-(4-methyl-1H-imidazol-1-yl)-5-(trifluoromethyl)phenyl)-3-(2-(2-(methylamino)pyrimidin-5-yl)ethynyl)benzamide (D800)

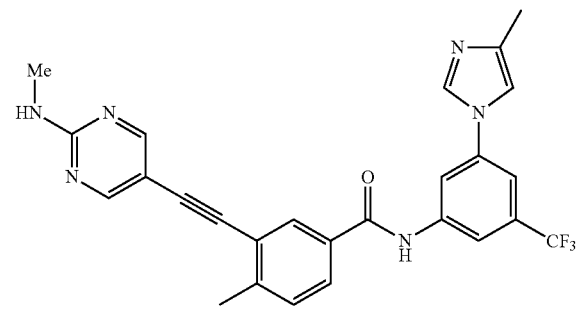 [SMILES: CNc1ncc(C#Cc2cc(C(=O)Nc3cc(-n4cnc(C)c4)cc(C(F)(F)F)c3)ccc2C)cn1]

The compound was synthesized by using the procedure similar to that of Example 1.

$^1$HNMR (400 MHz, d-DMSO), δ ppm 10.69 (s, 1H), 8.29 (m, 2H), 8.20-8.13 (m, 5H), 7.91 (d, J=4.8 Hz, 1H), 7.73-7.66 (m, 2H), 7.52 (m, 2H), 2.85 (d, J=4.4 Hz, 1H), 2.53 (s, 3H), 2.18 (s, 3H). MS (ESI), m/z: 491 (M$^+$+H$^+$).

Example 4

3-(2-(2-(ethylamino)pyrimidin-5-yl)ethynyl)-4-methyl-N-(3-(4-methyl-1H-imidazol-1-yl)-5-(trifluoromethyl)phenyl)benzamide (D755)

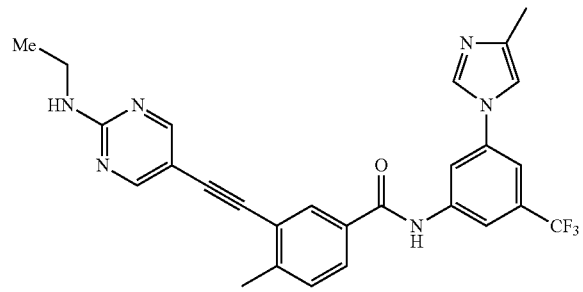 [SMILES: CCNc1ncc(C#Cc2cc(C(=O)Nc3cc(-n4cnc(C)c4)cc(C(F)(F)F)c3)ccc2C)cn1]

The compound was synthesized by using the procedure similar to that of Example 1.

$^1$HNMR (400 MHz, d-DMSO), δ ppm 10.69 (s, 1H), 8.52 (br, 2H), 8.29 (s, 1H), 8.21 (d, J=1.6 Hz, 1H), 8.16 (s, 1H), 8.13 (d, J=1.6 Hz, 1H), 7.91 (m, 1H), 7.75-7.73 (m, 2H), 7.52-7.49 (m, 2H), 3.35-3.29 (m, 2H), 2.52 (s, 3H), 2.18 (s, 3H), 1.15 (t, J=7.2 Hz, 3H). MS (ESI), m/z: 505 (M$^+$+H$^+$).

Example 5

4-methyl-N-(3-(4-methyl-1H-imidazol-1-yl)-5-(trifluoromethyl)phenyl)-3-(2-(2-(piperidin-1-yl)pyrimidin-5-yl)ethynyl)benzamide (D797)

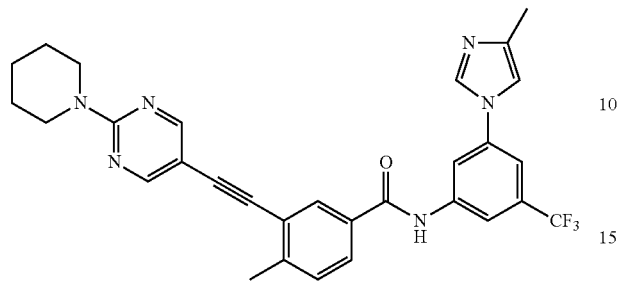

The compound was synthesized by using the procedure similar to that of Example 1.

$^1$HNMR (400 MHz, d-DMSO), δ 1.51 (4H, s), 1.62 (2H, s), 2.16 (3H, s), 3.77 (4H, s), 7.47 (2H, s), 7.70 (1H, s), 7.88 (1H, d, J=6.4 Hz), 8.15 (3H, m), 8.28 (1H, s), 8.53 (2H, s), 10.66 (1H, s). MS (ESI), m/z: 545 (M$^+$+H$^+$).

Example 6

3-(2-(6-aminopyridin-3-yl)ethynyl)-4-methyl-N-(3-(4-methyl-1H-imidazol-1-yl)-5-(trifluoromethyl)phenyl)benzamide (D827)

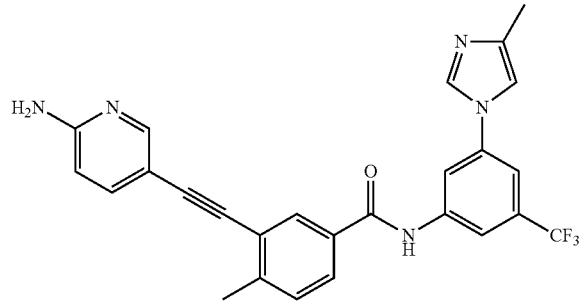 [SMILES: Cc1cn(-c2cc(NC(=O)c3ccc(C)c(C#Cc4ccc(N)nc4)c3)cc(C(F)(F)F)c2)cn1]

The compound was synthesized by using the procedure similar to that of Example 1.

$^1$HNMR (400 MHz, d-DMSO), δ 2.53 (3H, s), 6.48 (2H, s), 7.54 (2H, m), 7.74 (1H, s), 7.89 (1H, dd, J=8.0, 3.2 Hz), 8.13 (1H, d, J=1.6 Hz), 8.18 (2H, s), 8.31 (1.0H, s), 10.68 (1H, s). MS (ESI), m/z: 476 (M$^+$+H$^+$).

Example 7

3-(2-(2-(cyclopropylamino)pyrimidin-5-yl)ethynyl)-4-methyl-N-(4-((4-methylpiperazin-1-yl)methyl)-3-(trifluoromethyl)phenyl)benzamide (D825)

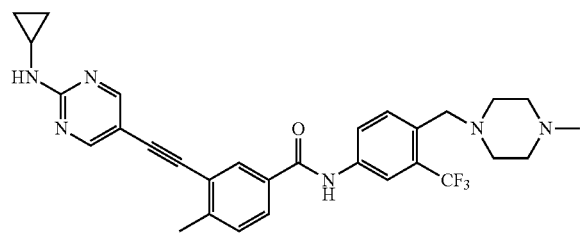 [SMILES: Cc1ccc(C(=O)Nc2ccc(CN3CCN(C)CC3)c(C(F)(F)F)c2)cc1C#Cc1cnc(NC2CC2)nc1]

The compound was synthesized by using the procedure similar to that of Example 1.

$^1$HNMR (400 MHz, d-DMSO), δ 0.51 (2H, s), 0.70 (2H, d, J=5.6 Hz), 2.42 (3H, s), 2.72 (3H, s), 2.75 (2H, m), 3.60 (6H, br), 7.48 (1H, d, J=7.8 Hz), 7.69 (1H, d, J=8.2 Hz), 7.89 (2H, m), 8.09 (2H, m), 8.21 (1H, s), 8.54 (2H, s), 10.51 (1H, s). MS (ESI), m/z: 549 (M$^+$+H$^+$).

Example 8

3-(2-(3H-imidazo[4,5-b]pyridin-6-yl)ethynyl)-4-methyl-N-(3-(4-methyl-1H-imidazol-1-yl)-5-(trifluoromethyl)phenyl)benzamide (D833)

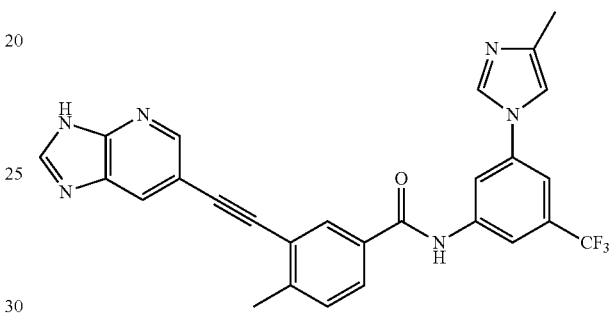

The compound was synthesized by using the procedure similar to that of Example 1.

$^1$HNMR (400 MHz, d-DMSO), δ 2.18 (3H, s), 2.60 (3H, s), 7.49 (1H, s), 7.55 (1H, d, J=8.0 Hz), 7.74 (1H, s), 7.94 (1H, d, J=7.8 Hz), 8.20 (4H, mHz), 8.30 (1H, s), 8.59 (1H, s), 10.72 (1H, s). MS (ESI), m/z: 501 (M$^+$+H$^+$).

Example 9

4-methyl-N-(4-((4-methylpiperazin-1-yl)methyl)-3-(trifluoromethyl)phenyl)-3-(2-(pyrazolo[1,5-a]pyrimidin-6-yl)ethynyl)benzamide (D856)

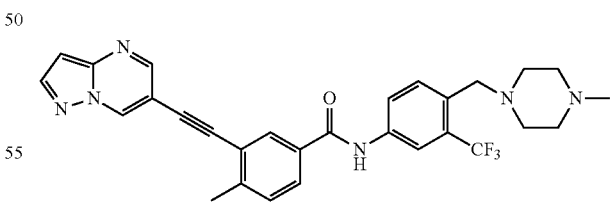

The compound was synthesized by using the procedure similar to that of Example 1.

$^1$HNMR (400 MHz, d-DMSO), δ 2.17 (3H, s), 2.37 (8H, m), 2.60 (3H, s), 3.57 (2H, s), 6.85 (1H, d, J=2.0 Hz), 7.54 (1H, d, J=8.0 Hz), 7.71 (1H, d, J=8.4 Hz), 7.96 (1H, dd, J=8.0, 3.29 Hz), 8.06 (1H, d, J=2.00 Hz), 8.21 (2H, dd, J=4.2, 2.0 Hz), 8.34 (1H, d, J=2.0 Hz), 8.72 (1H, d, J=2.0 Hz), 9.58 (1H, d, J=2.00 Hz), 10.56 (1H, s). MS (ESI), m/z: 533 (M$^+$+H$^+$).

Example 10

3-(2-(2-(cyclohexylamino)pyrimidin-5-yl)ethynyl)-4-methyl-N-(3-(4-methyl-1H-imidazol-1-yl)-5-(trifluoromethyl)phenyl)benzamide (D828)

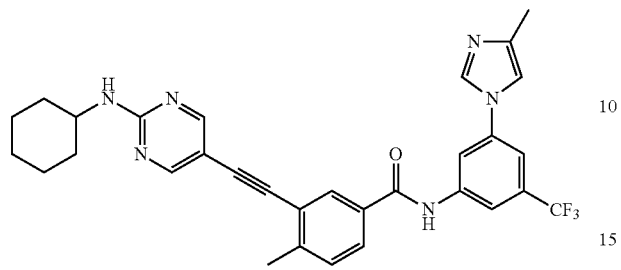

The compound was synthesized by using the procedure similar to that of Example 1.

¹HNMR (400 MHz, d-DMSO), δ 1.23 (4H, m), 1.71 (3H, m), 2.17 (2H, s), 2.54 (3H, s), 4.40 (1H, q, J=7.0 Hz), 7.51 (2H, m), 7.64 (1H, d, J=8.0 Hz), 7.72 (1H, s), 7.94 (1H, d, J=7.48 Hz), 8.14 (2H, m), 8.29 (1H, s), 8.49 (1H, s), 8.84 (1H, s), 10.68 (1H, s). MS (ESI), m/z: 559 (M⁺+H⁺).

Example 11

4-methyl-N-(3-(4-methyl-1H-imidazol-1-yl)-5-(trifluoromethyl)phenyl)-3-(2-(2-(phenylamino)pyrimidin-5-yl)ethynyl)benzamide (D809)

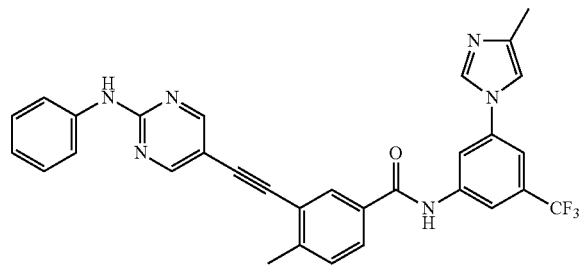 [SMILES: Cc1cn(-c2cc(NC(=O)c3ccc(C)c(C#Cc4cnc(Nc5ccccc5)nc4)c3)cc(C(F)(F)F)c2)cn1]

The compound was synthesized by using the procedure similar to that of Example 1.

¹HNMR (400 MHz, d-DMSO), δ 2.18 (3H, s), 2.56 (3H, s), 7.02 (1H, t, J=7.2 Hz), 7.32 (2.0H, t, J=8.0 Hz), 7.49 (1H, s), 7.54 (1H, d, J=8.0 Hz), 7.75 (3H, m), 7.93 (1H, dd, J=8.0, 3.2 Hz), 8.17 (2H, s), 8.21 (1H, s), 8.30 (1H, s), 8.72 (2H, s), 10.06 (1H, s), 10.71 (1H, s). MS (ESI), m/z: 553 (M⁺+H⁺).

Example 12

3-(2-(1H-pyrrolo[2,3-b]pyridin-5-yl)ethynyl)-4-methyl-N-(3-(4-methyl-1H-imidazol-1-yl)-5-(trifluoromethyl)phenyl)benzamide (D832)

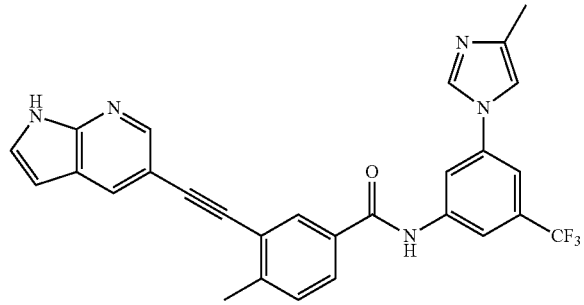 [SMILES: Cc1cn(-c2cc(NC(=O)c3ccc(C)c(C#Cc4cnc5[nH]ccc5c4)c3)cc(C(F)(F)F)c2)cn1]

The compound was synthesized in a similar procedure of Example 8.

¹HNMR (400 MHz, d-DMSO), δ 2.18 (3H, s), 2.58 (3H, s), 6.53 (1H, q, J=1.71 Hz), 7.53 (3H, m), 7.73 (1H, s), 7.92 (1H, dd, J=8.0, 3.2 Hz), 8.20 (3H, m), 8.31 (1H, s), 8.46 (1H, s), 10.70 (1H, s), 11.95 (1H, s). MS (ESI), m/z: 500 (M⁺+H⁺).

Example 13

3-(2-(2-(2-hydroxyethylamino)pyrimidin-5-yl)ethynyl)-4-methyl-N-(3-(4-methyl-1H-imidazol-1-yl)-5-(trifluoromethyl)phenyl)benzamide (D820)

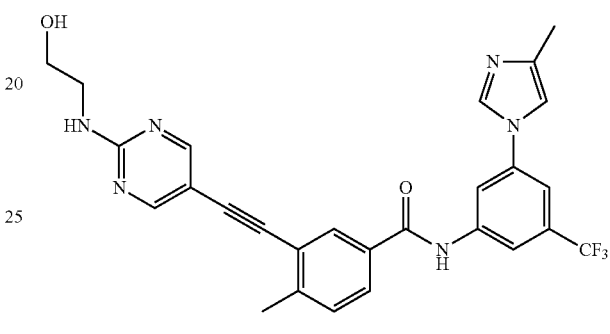

The compound was synthesized by using the procedure similar to that of Example 1.

¹HNMR (400 MHz, d-DMSO), δ 2.19 (3H, s), 2.53 (3H, s), 3.15 (1H, m), 3.41 (2H, m), 3.53 (2H, m), 4.73 (1H, t, J=5.2 Hz), 7.52 (1H, d, J=8.0 Hz), 7.63 (1H, s), 7.74 1H, s), 7.91 (1H, m), 8.00 (1H, s), 8.16 (2H, m), 8.31 (1H, s), 8.52 (1H, s), 10.71 (1H, s). MS (ESI), m/z: 521 (M⁺+H⁺).

Example 14

N-(3-(1H-imidazol-1-yl)-5-(trifluoromethyl)phenyl)-4-methyl-3-(2-(pyrazolo[1,5-a]pyrimidin-6-yl)ethynyl)benzamide (D819)

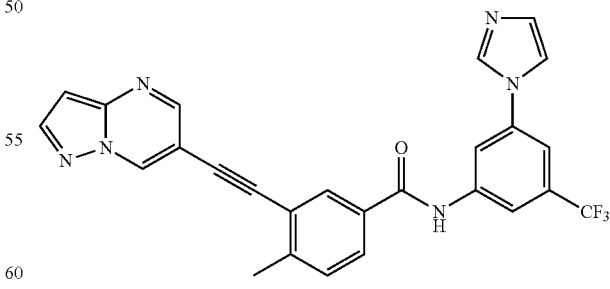

The compound was synthesized by using the procedure similar to that of Example 1.

¹HNMR (400 MHz, d-DMSO), δ 2.61 (3H, s), 6.85 (1.0H, d, J=2.0 Hz), 7.21 (1H, s), 7.57 (1H, d, J=8.4 Hz), 7.82 (2H, m), 7.98 (1H, dd, J=8.0, 3.2 Hz), 8.23 (2H, m), 8.35 (3H, d,

J=2.4 Hz), 8.73 (1H, d, J=2.00 Hz), 9.59 (1H, d, J=2.0 Hz), 10.77 (1H, s). MS (ESI), m/z: 487 (M$^+$+H$^+$).

Example 15

4-methyl-N-(3-(3-methyl-1H-1,2,4-triazol-1-yl)-5-(trifluoromethyl)phenyl)-3-(2-(pyrazolo[1,5-a]pyrimidin-6-yl) ethynyl)benzamide (D818)

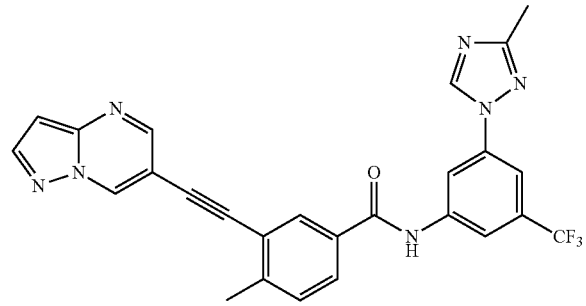 [SMILES: Cc1ncn(-c2cc(NC(=O)c3ccc(C)c(C#Cc4cnc5ccnn5c4)c3)cc(C(F)(F)F)c2)n1]

The compound was synthesized by using the procedure similar to that of Example 1.

$^1$HNMR (400 MHz, d-DMSO), δ 2.40 (3H, s), 2.60 (3H, s), 6.85 (1H, d, J=1.6 Hz), 7.56 (1H, d, J=8.2 Hz), 7.99 (2H, m), 8.26 (2H, m), 8.35 (1H, d, J=2.0 Hz), 8.64 (1H, s), 8.73 (1H, d, J=2.0 Hz), 9.32 (1H, s), 9.58 (1H, d, J=1.2 Hz), 10.80 (1H, s). MS (ESI), m/z: 502 (M$^+$+H$^+$).

Example 16

3-(2-(imidazo[1,2-a]pyrimidin-6-yl)ethynyl)-4-methyl-N-(3-(4-methyl-1H-imidazol-1-yl)-5-(trifluoromethyl)phenyl)benzamide (D799)

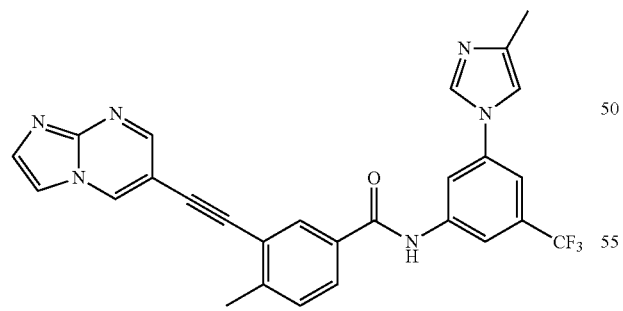

The compound was synthesized by using the procedure similar to that of Example 1.

$^1$HNMR (400 MHz, d-DMSO), δ 2.19 (3H, s), 2.59 (3H, s), 7.50 (1H, s), 7.57 (1H, d, J=8.2 Hz), 7.74 (1H, s), 7.82 (1H, s), 7.97 (2H, m), 8.17 (1H, s), 8.22 (2H, d, J=2.0 Hz), 8.31 (1H, s), 8.71 (1H, d, J=2.4 Hz), 9.40 (1H, d, J=2.4 Hz), 10.73 (1H, s). MS (ESI), m/z: 501 (M$^+$+H$^+$).

Example 17

3-(2-(1H-pyrazolo[3,4-b]pyridin-5-yl)ethynyl)-4-methyl-N-(3-(4-methyl-1H-imidazol-1-yl)-5-(trifluoromethyl)phenyl)benzamide (D767)

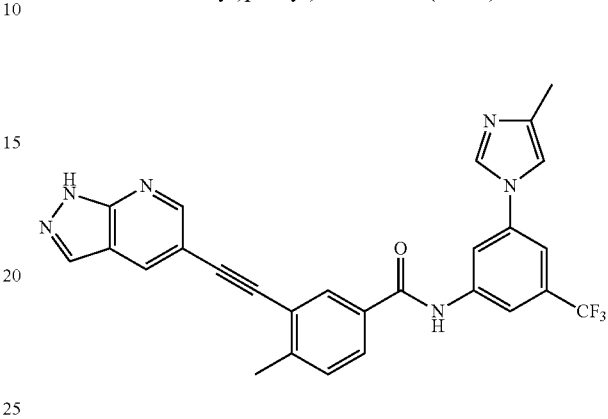

The compound was synthesized by using the procedure similar to that of Example 1.

$^1$HNMR (400 MHz, d-DMSO), δ 13.95 (s, 1H), 10.72 (s, 1H), 8.75 (s, 1H), 8.54 (s, 1H), 8.31 (s, 1H), 8.23 (s, 3H), 8.18 (s, 1H), 7.97 (d, J=8.0 Hz, 1H), 7.75 (s, 1H), 7.57 (d, J=8.0 Hz, 1H), 7.49 (s, 1H), 2.60 (s, 3H), 2.19 (s, 3H). MS (ESI), m/z: 501 (M$^+$+H$^+$).

Example 18

N-(3-(1H-imidazol-1-yl)-5-(trifluoromethyl)phenyl)-3-(2-(1H-pyrazolo[3,4-b]pyridin-5-yl)ethynyl)-4-methylbenzamide (D831)

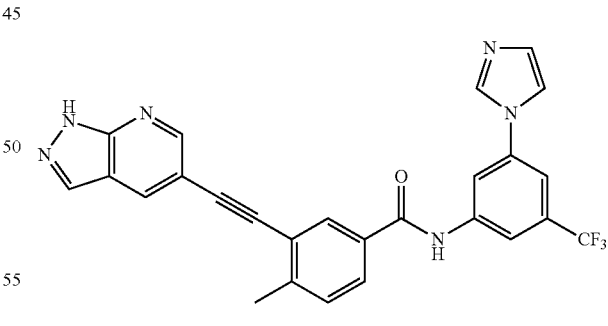

The compound was synthesized by using the procedure similar to that of Example 1.

$^1$HNMR (400 MHz, d-DMSO), δ 13.92 (s, 1H), 10.72 (s, 1H), 8.72 (d, J=2.0 Hz, 1H), 8.51 (d, J=2.0 Hz, 1H), 8.32 (s, 2H), 8.21 (s, 3H), 7.95 (d, J=8.0 Hz, 1H), 7.79 (d, J=4.0 Hz, 2H), 7.54 (d, J=8.0 Hz, 1H), 7.16 (s, 1H), 2.58 (s, 3H). MS (ESI), m/z: 487 (M$^+$+H$^+$).

Example 19

3-(2-(1H-pyrazolo[3,4-b]pyridin-5-yl)ethynyl)-4-methyl-N-(3-(3-methyl-1H-1,2,4-triazol-1-yl)-5-(trifluoromethyl)phenyl)benzamide (D835)

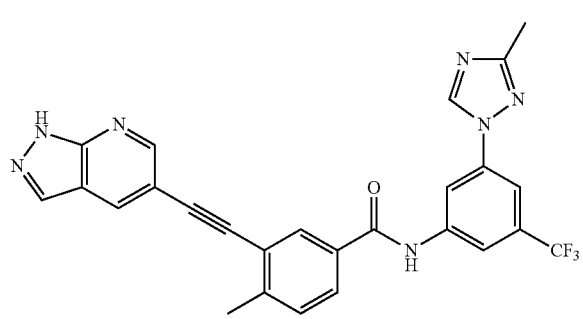 [SMILES: Cc1cn(-c2cc(NC(=O)c3ccc(C)c(C#Cc4cnc5[nH]ncc5c4)c3)cc(C(F)(F)F)c2)cn1]

The compound was synthesized by using the procedure similar to that of Example 1.

$^1$HNMR (400 MHz, d-DMSO), δ 13.92 (s, 1H), 10.76 (s, 1H), 9.30 (s, 1H), 8.73 (d, J=2.0 Hz, 1H), 8.63 (s, 1H), 8.52 (d, J=2.0 Hz, 1H), 8.26 (m, 3H), 7.97 (m, 2H), 7.55 (d, J=8.0 Hz, 1H), 2.58 (s, 3H), 2.38 (s, 3H). MS (ESI), m/z: 502 (M$^+$+H$^+$).

Example 20

3-(2-([1,2,4]-triazolo[1,5-a]pyrimidin-6-yl)ethynyl)-4-methyl-N-(3-(4-methyl-1H-imidazol-1-yl)-5-(trifluoromethyl)phenyl)benzamide (D798)

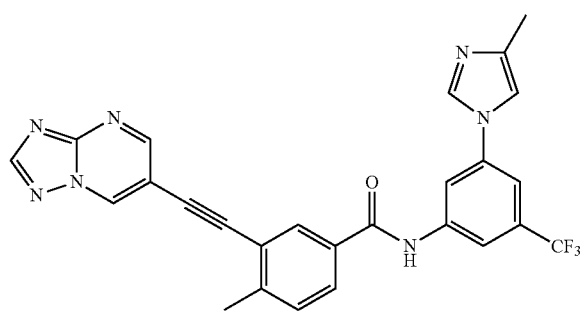 [SMILES: Cc1cn(-c2cc(NC(=O)c3ccc(C)c(C#Cc4cnc5ncnn5c4)c3)cc(C(F)(F)F)c2)cn1]

The compound was synthesized by using the procedure similar to that of Example 1.

$^1$HNMR (400 MHz, d-DMSO), δ 2.17 (3H, s), 2.60 (3H, s), 7.48 (1H, s), 7.58 (1H, d, J=8.4 Hz), 7.74 (1H, s), 7.98 (1H, d, J=8.0 Hz), 8.15 (1H, s), 8.22 (2H, m), 8.29 (1H, s), 8.78 (1H, s), 9.09 (1H, d, J=2.4 Hz), 9.88 (1H, d, J=2.4 Hz), 10.74 (1H, s). MS (ESI), m/z: 502 (M$^+$+H$^+$.

Example 21

4-methyl-N-(3-(4-methyl-1H-imidazol-1-yl)-5-(trifluoromethyl)phenyl)-3-(2-(pyrazolo[1,5-a]pyrimidin-6-yl)ethynyl)benzamide (D822)

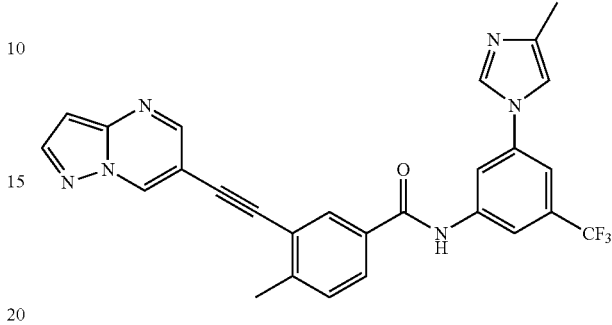

The compound was synthesized by using the procedure similar to that of Example 1.

$^1$HNMR (400 MHz, d-DMSO), δ 2.18 (3H, s), 2.59 (3H, s), 6.84 (1H, m), 7.49 (1H, s), 7.57 (1H, d, J=8.4 Hz), 7.73 (1H, s), 7.98 (1H, dd, J=8.0, 1.6 Hz), 8.16 (1H, s), 8.21 (2H, d, J=2.0 Hz), 8.28 (1H, s), 8.34 (1H, d, J=2.4 Hz), 8.71 (1H, d, J=2.4 Hz), 9.57 (1H, d, J=2.0 Hz), 10.74 (1H, s). MS (ESI), m/z: 502 (M$^+$+H$^+$).

Example 22

3-(2-(1H-pyrazolo[3,4-b]pyridin-5-yl)ethynyl)-4-methyl-N-(3-(trifluoromethyl)phenyl)benzamide (D821)

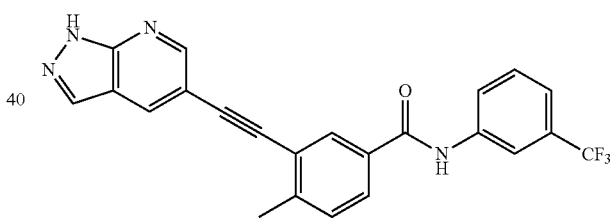

The compound was synthesized by using the procedure similar to that of Example 1.

$^1$HNMR (400 MHz, d-DMSO), δ 13.94 (s, 1H), 10.59 (s, 1H), 8.75 (d, J=2.0 Hz, 1H), 8.54 (d, J=2.0 Hz, 1H), 8.26 (m, 3H), 8.10 (d, J=8.0 Hz, 1H), 7.95 (dd, J=8.0, 2.0 Hz, 1H), 7.64 (m, 3H), 2.59 (s, 3H). MS (ESI), m/z: 421 (M$^+$+H$^+$).

Example 23

3-(2-(1H-pyrazolo[3,4-b]pyridin-5-yl)ethynyl)-4-methyl-N-(4-((4-methylpiperazin-1-yl)methyl)-3-(trifluoromethyl)phenyl)benzamide (D824)

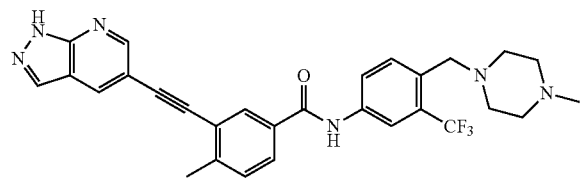 [SMILES: Cc1ccc(C(=O)Nc2ccc(CN3CCN(C)CC3)c(C(F)(F)F)c2)cc1C#Cc1cnc2[nH]ncc2c1]

The compound was synthesized by using the procedure similar to that of Example 1.

¹HNMR (400 MHz, d-DMSO), δ 13.92 (s, 1H), 10.55 (s, 1H), 8.72 (d, J=2.0 Hz, 1H), 8.52 (d, J=2.0 Hz, 1H), 8.17 (m, 3H), 8.10 (d, J=8.0 Hz, 1H), 7.92 (dd, J=8.0, 2.0 Hz, 1H), 7.70 (d, J=8.8 Hz, 1H), 7.53 (d, J=8.0 Hz, 1H), 3.80 (s, 2H), 3.10 (brs, 8H), 2.71 (s, 3H), 2.57 (s, 3H). MS (ESI), m/z: 533, (M⁺+H⁺).

Example 24

3-(2-(2-((S)-2,3-dihydroxypropylamino)pyrimidin-5-yl)ethynyl)-4-methyl-N-(3-(4-methyl-1H-imidazol-1-yl)-5-(trifluoromethyl)phenyl)benzamide (D834)

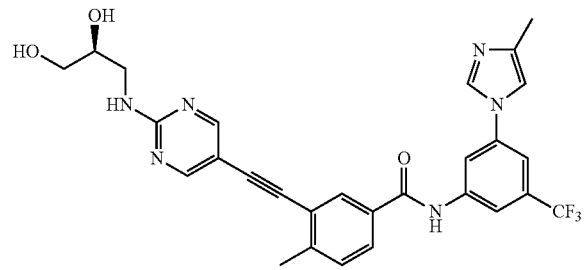 [SMILES: Cc1cn(-c2cc(NC(=O)c3ccc(C)c(C#Cc4cnc(NC[C@H](O)CO)nc4)c3)cc(C(F)(F)F)c2)cn1]

The compound was synthesized by using the procedure similar to that of Example 1.

¹HNMR (400 MHz, d-DMSO), δ 2.31 (3H, s), 2.98 (1H, s), 3.65 (2H, br), 4.57 (1H, s), 4.78 (1H, s), 7.49 (4H, br), 7.70 (1H, br), 7.99 (2H, m), 8.22 (4H, s), 8.50 (2H, s), 10.67 (1H, s). MS (ESI), m/z: 551 (M⁺+H⁺).

Example 25

3-(2-(2-(diethylamino)pyrimidin-5-yl)ethynyl)-4-methyl-N-(3-(4-methyl-1H-imidazol-1-yl)-5-(trifluoromethyl)phenyl)benzamide (D807)

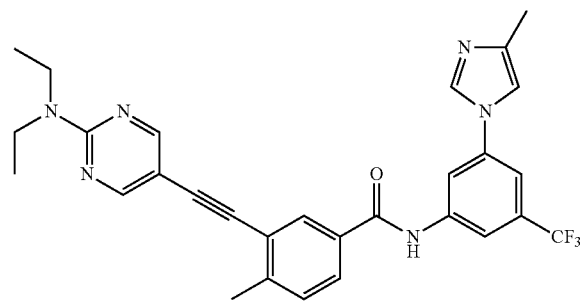 [SMILES: CCN(CC)c1ncc(C#Cc2cc(C(=O)Nc3cc(-n4cnc(C)c4)cc(C(F)(F)F)c3)ccc2C)cn1]

The compound was synthesized by using the procedure similar to that of Example 1.

¹HNMR (400 MHz, d-DMSO), δ ppm 10.65 (s, 1H), 8.54 (br, 2H), 8.29 (s, 1H), 8.18 (m, 3H), 7.88 (d, J=7.2 Hz, 1H), 7.70 (s, 1H), 7.48 (m, 2H), 3.62 (m, 4H), 2.52 (s, 3H), 2.17 (s, 3H), 1.17 (t, J=7.2 Hz, 6H). MS (ESI), m/z: 533 (M⁺+H⁺).

Example 26

3-(2-(2-(tert-butylamino)pyrimidin-5-yl)ethynyl)-4-methyl-N-(3-(4-methyl-1H-imidazol-1-yl)-5-(trifluoromethyl)phenyl)benzamide (D806)

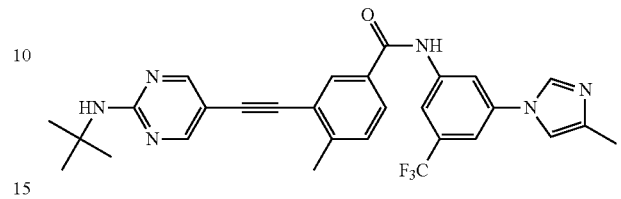

The compound was synthesized by using the procedure similar to that of Example 1.

¹HNMR (400 MHz, d-DMSO), δ 10.69 (s, 1H), 8.51 (s, 2H), 8.29 (s, 1H), 8.20 (s, 1H), 8.16 (s, 1H), 8.12 (s, 1H), 7.91 (dd, J=6.8, 1.6 Hz, 1H), 7.73 (s, 1H), 7.52 (m, 2H), 7.38 (s, 1H), 2.55 (s, 3H), 2.18 (s, 3H), 1.39 (s, 9H). MS (ESI), m/z: 533, (M⁺+H⁺).

Example 27

3-(2-(2-(isopropylamino)pyrimidin-5-yl)ethynyl)-4-methyl-N-(3-(4-methyl-1H-imidazol-1-yl)-5-(trifluoromethyl)phenyl)benzamide (D752)

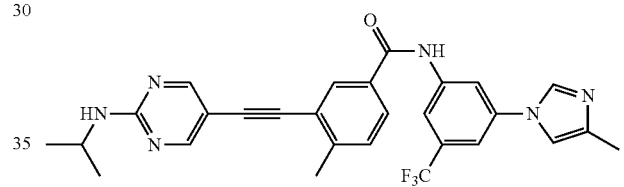

The compound was synthesized by using the procedure similar to that of Example 1.

¹HNMR (400 MHz, d-DMSO), δ 10.69 (s, 1H), 8.51 (s, 2H), 8.29 (s, 1H), 8.20 (s, 1H), 8.16 (s, 1H), 8.12 (s, 1H), 7.91 (dd, J=6.8, 1.6 Hz, 1H), 7.73 (s, 1H), 7.52 (d, J=8.0 Hz, 1H), 7.50 (m, 2H), 4.08 (m, 1H), 2.51 (s, 3H), 2.18 (s, 3H), 1.17 (d, J=6.4 Hz, 6H). MS (ESI), m/z: 519, (M⁺+H⁺.

Example 28

3-(2-(2-aminopyrimidin-5-yl)ethynyl)-4-methyl-N-(3-(4-methyl-1H-imidazol-1-yl)-5-(trifluoromethyl)phenyl)benzamide (D803)

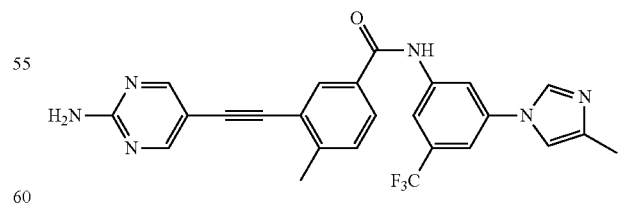

The compound was synthesized by using the similar procedure similar to that of Example 1.

¹HNMR (400 MHz, d-DMSO), δ 10.69 (s, 1H), 8.48 (s, 2H), 8.31 (m, 2H), 8.16 (s, 1H), 8.13 (s, 1H), 7.91 (d, J=7.2 Hz, 1H), 7.74 (s, 1H), 7.51 (s, 2H), 7.20 (m, 2H), 2.52 (s, 3H), 2.19 (s, 3H). MS (ESI), m/z: 477, (M⁺+H⁺).

Example 29

4-methyl-N-(4-(morpholinomethyl)-3-(trifluoromethyl)phenyl)-3-(2-(pyrazolo[1,5-a]pyrimidin-6-yl)ethynyl)benzamide (D931)

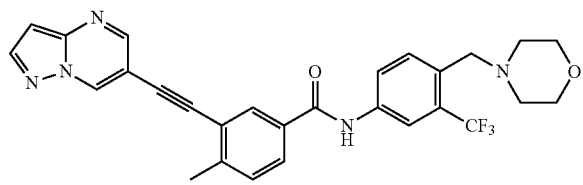 [SMILES: Cc1ccc(C(=O)Nc2ccc(CN3CCOCC3)c(C(F)(F)F)c2)cc1C#Cc1cnc2ccnn2c1]

The compound was synthesized by using the procedure similar to that of Example 1.

$^1$HNMR (400 MHz, d-DMSO), δ 2.39 (4H, brs), 2.59 (3H, s), 3.61 (6H, m), 6.85 (1H, s), 7.55 (1H, d, J=8.4 Hz), 7.72 (1H, d, J=8.4 Hz), 7.94 (1H, dd, J=8.0, 1.6 Hz), 8.06 (1H, d, J=8.4 Hz), 8.21 (2H, dd, J=4.2, 1.6 Hz), 8.34 (1H, d, J=6.0 Hz), 8.72 (1H, d, J=2.0 Hz), 9.58 (1H, d, J=1.2 Hz), 10.56 (1H, s). MS (ESI), m/z: 520 (M$^+$+H$^+$).

Example 30

N-(4-((4-(2-hydroxyethyl)piperazin-1-yl)methyl)-3-(trifluoromethyl)phenyl)-4-methyl-3-(2-(pyrazolo[1,5-a]pyrimidin-6-yl)ethynyl)benzamide (D942)

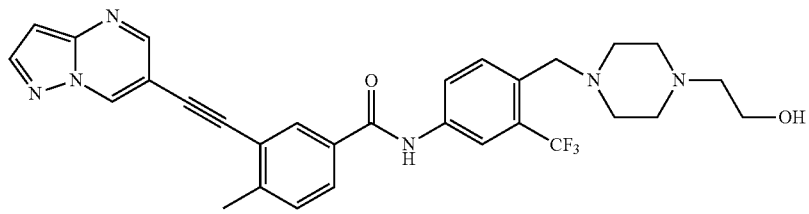 [SMILES: Cc1ccc(C(=O)Nc2ccc(CN3CCN(CCO)CC3)c(C(F)(F)F)c2)cc1C#Cc1cnc2ccnn2c1]

The compound was synthesized by using the procedure similar to that of Example 1.

$^1$HNMR (400 MHz, d-DMSO), δ 2.39 (10H, m), 2.59 (3H, s), 3.49 (2H, m), 3.56 (2H, s), 4.36 (1H, br), 6.85 (1H, s), 7.55 (1H, d, J=8.0 Hz), 7.72 (1H, d, J=8.8 Hz), 7.94 (1H, dd, J=8.0, 1.6 Hz), 8.05 (1H, d, J=8.4 Hz), 8.21 (2H, dd, J=4.8, 1.6 Hz), 8.34 (1H, d, J=2.0 Hz), 8.72 (1H, d, J=2.0 Hz), 9.58 (1H, d, J=1.2 Hz), 10.55 (1H, s). MS (ESI), m/z: 563 (M$^+$+H$^+$.

Example 31

(S)—N-(4-((3-(dimethylamino)pyrrolidin-1-yl)methyl)-3-(trifluoromethyl)phenyl)-4-methyl-3-(2-(pyrazolo[1,5-a]pyrimidin-6-yl)ethynyl)benzamide (D940)

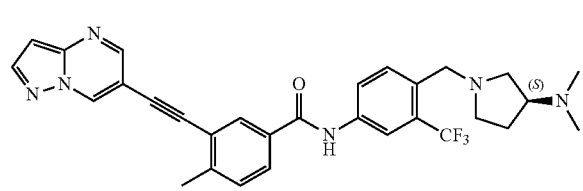

The compound was synthesized by using the procedure similar to that of Example 1.

$^1$HNMR (400 MHz, d-DMSO), δ 1.62 (1H, m), 1.85 (1H, m), 2.12 (6H, s), 2.38 (1H, m), 2.59 (4H, m), 2.61 (1H, m), 2.83 (1H, m), 3.36 (2H, m), 3.56 (2H, s), 6.84 (1H, s), 7.55 (1H, d, J=8.0 Hz), 7.72 (1H, d, J=8.8 Hz), 7.94 (1H, dd, J=8.0, 1.6 Hz), 8.05 (1H, d, J=8.4 Hz), 8.19 (2H, s), 8.34 (1H, d, J=2.4 Hz), 8.72 (1H, d, J=2.0 Hz), 9.56 (1H, d, J=1.2 Hz), 10.55 (1H, s). MS (ESI), m/z: 547 (M$^+$+H$^+$).

Example 32

N-(3-tert-butyl-5-(4-methyl-1H-imidazol-1-yl)phenyl)-4-methyl-3-(2-(pyrazolo[1,5-a]pyrimidin-6-yl)ethynyl)benzamide (D941)

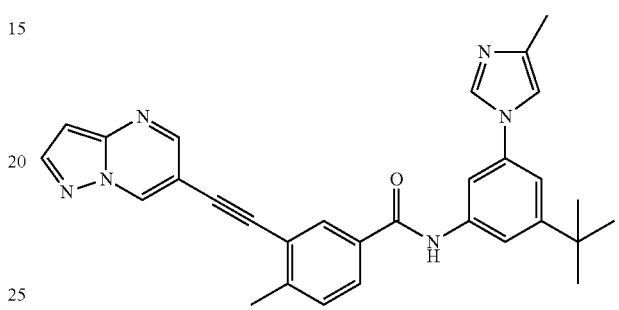

The compound was synthesized by using the procedure similar to that of Example 1.

$^1$HNMR (400 MHz, d-DMSO), δ 1.34 (9H, s), 2.18 (3H, s), 2.59 (3H, m), 6.84 (1H, s), 7.30 (1H, s), 7.40 (1H, br), 7.55 (1H, d, J=8.0 Hz), 7.38 (1H, s), 7.97 (2H, m), 8.08 (1H, br), 8.21 (1H, d, J=1.6 Hz), 8.34 (1H, d, J=2.4 Hz), 8.72 (1H, d, J=2.0 Hz), 9.57 (1H, d, J=1.2 Hz), 10.42 (1H, s). MS (ESI), m/z: 489 (M$^+$+H$^+$).

Example 33

3-(2-(1H-pyrazolo[3,4-b]pyridin-5-yl)ethynyl)-4-methyl-N-(3-(4-methyl-1H-imidazol-1-yl)phenyl)benzamide (D967)

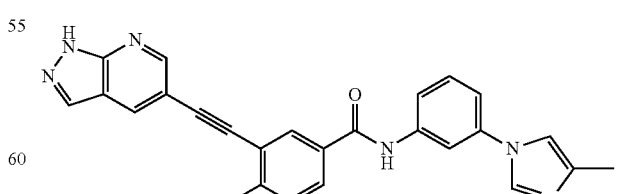

The compound was synthesized by using the procedure similar to that of Example 1.

$^1$HNMR (400 MHz, d-DMSO), 13.95 (s, 1H), 10.47 (s, 1H), 8.74 (s, 1H), 8.52 (s, 1H), 8.22 (m, 2H), 8.06 (m, 2H), 7.94 (d, J=7.6 Hz, 1H), 7.76 (d, J=8.0 Hz, 1H), 7.53 (m, 2H), 7.35 (m, 2H), 2.59 (s, 3H), 2.18 (s, 3H). MS (ESI), m/z: 433 (M++H+).

Example 34

3-(2-(1H-pyrazolo[3,4-b]pyridin-5-yl)ethynyl)-N-(3-tert-butyl-5-(4-methyl-1H-imidazol-1-yl)phenyl)-4-methylbenzamide (D968)

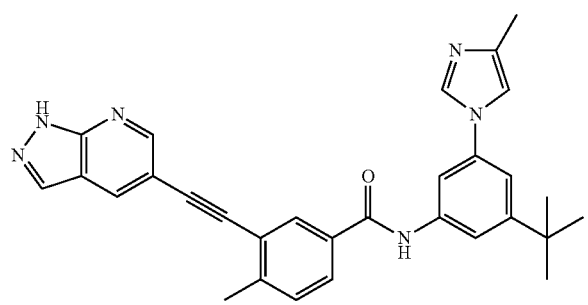 [SMILES: Cc1cn(-c2cc(NC(=O)c3ccc(C)c(C#Cc4cnc5[nH]ncc5c4)c3)cc(C(C)(C)C)c2)cn1]

The compound was synthesized by using the procedure similar to that of Example 1.

¹HNMR (400 MHz, d-DMSO), δ 13.95 (s, 1H), 10.42 (s, 1H), 8.75 (s, 1H), 8.54 (s, 1H), 8.23 (m, 2H), 8.07 (s, 1H), 7.96 (m, 2H), 7.75 (s, 1H), 7.54 (d, J=8.0 Hz, 1H), 7.31 (s, 2H), 7.30 (d, J=4.2 Hz, 1H), 2.59 (s, 3H), 2.18 (s, 3H), 1.34 (s, 9H). MS (ESI), m/z: 489 (M++H+).

Example 35

3-(2-(1H-pyrazolo[3,4-b]pyridin-5-yl)ethynyl)-N-(3-fluoro-5-(4-methyl-1H-imidazol-1-yl)phenyl)-4-methylbenzamide (D963)

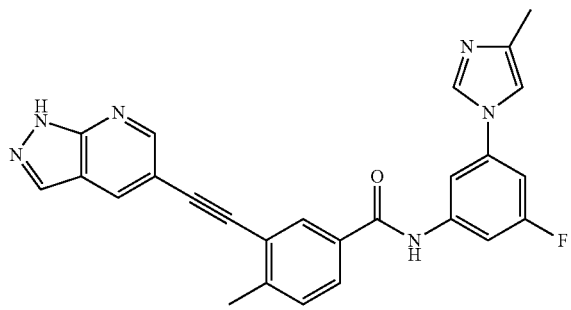 [SMILES: Cc1cn(-c2cc(F)cc(NC(=O)c3ccc(C)c(C#Cc4cnc5[nH]ncc5c4)c3)c2)cn1]

The compound was synthesized by using the procedure similar to that of Example 1.

¹HNMR (400 MHz, d-DMSO), δ 13.94 (s, 1H), 10.58 (s, 1H), 8.74 (s, 1H), 8.51 (s, 1H), 8.22 (d, J=8.0 Hz, 2H), 8.11 (s, 1H), 7.93 (d, J=7.6 Hz, 1H), 7.83 (s, 1H), 7.71 (d, J=7.2 Hz, 1H), 7.54 (d, J=8.0 Hz, 1H), 7.39 (s, 1H), 7.33 (d, J=10 Hz, 1H), 2.58 (s, 3H), 2.17 (s, 3H). MS (ESI), m/z: 451 (M++H+).

Example 36

3-(2-(1H-pyrazolo[3,4-b]pyridin-5-yl)ethynyl)-N-(3-chloro-5-(4-methyl-1H-imidazol-1-yl)phenyl)-4-methylbenzamide (D964)

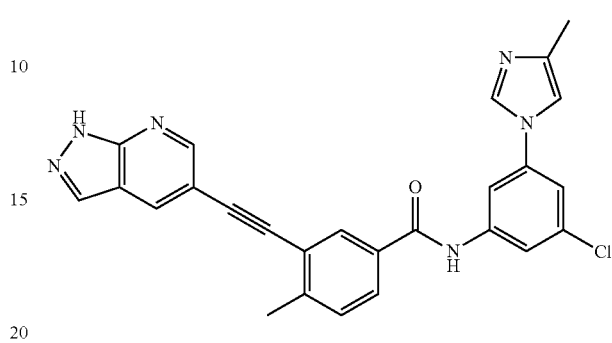

The compound was synthesized by using the procedure similar to that of Example 1.

¹HNMR (400 MHz, d-DMSO), δ 13.94 (s, 1H), 10.52 (s, 1H), 8.78 (s, 1H), 8.48 (s, 1H), 8.21 (s, 1H), 8.16 (s, 1H), 8.11 (s, 1H), 7.95 (s, 1H), 7.88 (s, 2H), 7.49 (s, 2H), 7.36 (s, 1H), 2.57 (s, 3H), 2.15 (s, 3H). MS (ESI), m/z: 468 (M++H+.

Example 37

(R)—N-(4-(3-(dimethylamino)pyrrolidin-1-yl)methyl)-3-(trifluoromethyl)phenyl)-4-methyl-3-(2-(pyrazolo[1,5-a]pyrimidin-6-yl)ethynyl)benzamide (D943)

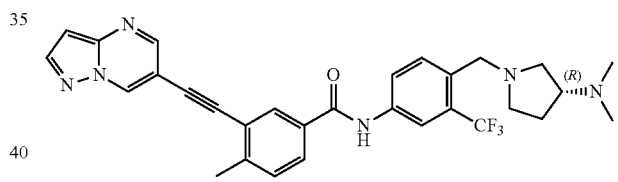

The compound was synthesized by using the procedure similar to that of Example 1.

¹HNMR (400 MHz, d-DMSO), δ 1.62 (1H, m), 1.85 (1H, m), 2.12 (6H, s), 2.37 (1H, m), 2.59 (4H, m), 2.61 (1H, m), 2.83 (1H, m), 3.36 (2H, m), 3.56 (2H, s), 6.84 (1H, s), 7.55 (1H, d, J=8.0 Hz), 7.73 (1H, d, J=8.8 Hz), 7.95 (1H, dd, J=8.0, 1.6 Hz), 8.05 (1H, d, J=8.4 Hz), 8.19 (2H, s), 8.34 (1H, d, J=2.4 Hz), 8.72 (1H, d, J=2.0 Hz), 9.56 (1H, d, J=1.2 Hz), 10.55 (1H, s). MS (ESI), m/z: 547 (M++H+).

Example 38

(S)-3-(2-(1H-pyrazolo[3,4-b]pyridin-5-yl)ethynyl)-N-(4-((3-(dimethylamino)pyrrolidin-1-yl)methyl)-3-(trifluoromethyl)phenyl)-4-methylbenzamide (D966)

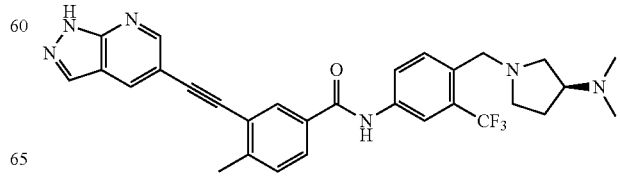

The compound was synthesized by using the procedure similar to that of Example 1.

¹HNMR (400 MHz, d-DMSO), δ 13.95 (s, 1H), 10.55 (s, 1H), 8.75 (s, 1H), 8.54 (s, 1H), 8.24 (m, 3H), 8.09 (d, J=8.4 Hz, 1H), 7.95 (d, J=8.4 Hz, 1H), 7.72 (d, J=8.4 Hz, 1H), 7.55 (d, J=8.0 Hz, 1H), 3.74 (m, 2H), 3.52 (m, 1H), 3.17 (s, 1H), 2.88 (br, 1H), 2.68 (m, 1H), 2.59 (s, 3H), 2.43 (m, 1H), 2.17 (s, 6H), 1.91 (s, 4H), 1.70 (m, 2H). MS (ESI), m/z: 547 (M⁺+H⁺).

Example 39

(R)-3-(2-(1H-pyrazolo[3,4-b]pyridin-5-yl)ethynyl)-N-(4-((3-(dimethylamino)pyrrolidin-1-yl)methyl)-3-(trifluoromethyl)phenyl)-4-methylbenzamide (D965)

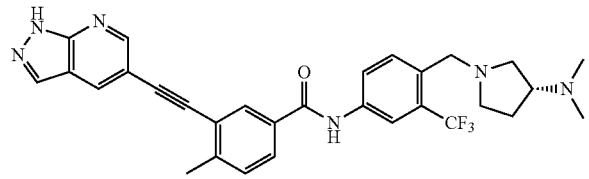 [SMILES: Cc1ccc(C(=O)Nc2ccc(CN3CC[C@@H](N(C)C)C3)c(C(F)(F)F)c2)cc1C#Cc1cnc2[nH]ncc2c1]

The compound was synthesized by using the procedure similar to that of Example 1.

¹HNMR (400 MHz, d-DMSO), δ 13.95 (s, 1H), 10.55 (s, 1H), 8.76 (s, 1H), 8.54 (s, 1H), 8.24 (m, 3H), 8.09 (d, J=8.4 Hz, 1H), 7.94 (d, J=8.4 Hz, 1H), 7.72 (d, J=8.4 Hz, 1H), 7.54 (d, J=8.0 Hz, 1H), 3.74 (m, 2H), 3.51 (m, 1H), 3.17 (s, 1H), 2.88 (br, 1H), 2.68 (m, 1H), 2.59 (s, 3H), 2.43 (m, 1H), 2.17 (s, 6H), 1.91 (s, 4H), 1.71 (m, 2H). MS (ESI), m/z: 547 (M⁺+H⁺).

Example 40

3-(2-(1H-pyrazolo[3,4-b]pyridin-5-yl)ethynyl)-N-(4-((4-methylpiperazin-1-yl)methyl)-3-(trifluoromethyl)phenyl)benzamide D1072)

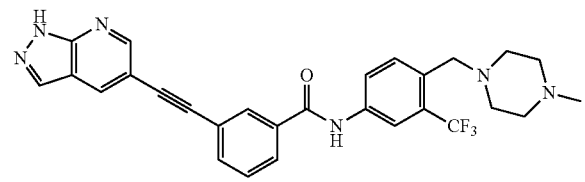 [SMILES: CN1CCN(Cc2ccc(NC(=O)c3cccc(C#Cc4cnc5[nH]ncc5c4)c3)cc2C(F)(F)F)CC1]

The compound was synthesized by using the procedure similar to that of Example 1.

¹HNMR (400 MHz, d-DMSO), δ 10.62 (s, 1H), 8.73 (d, J=2.0 Hz, 1H), 8.52 (d, J=2.0 Hz, 1H), 8.21-8.23 (m, 3H), 8.07 (d, J=8.4 Hz, 1H), 8.01 (d, J=7.6 Hz, 1H), 7.83 (d, J=7.6 Hz, 1H), 7.72 (d, J=7.6 Hz, 1H), 7.64 (t, J=8.0 Hz, 1H), 3.57 (s, 2H), 2.39 (br, 8H), 2.16 (s, 3H). MS (ESI), m/z: 519 (M⁺+H⁺).

Example 41

3-(2-(1H-pyrazolo[3,4-b]pyridin-5-yl)ethynyl)-4-methyl-N-(4-((4-methylpiperazin-1-yl)methyl)-3-(trifluoromethyl)phenyl)benzamide dimesylate (D824 dimesylate)

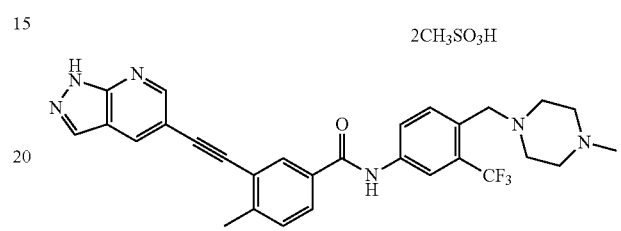

Add 2.24 g methanesulfonic acid (23.31 mmol) drop wise into 3.1 g D824 (5.83 mmol) in 150 mL ethanol into in a 500 mL round flask. The reaction mixture turns clear when heated to boiling. After refluxing for 4 h, the reaction is cooled to room temperature, And white solid is collected and washed three times with ethanol after filtration. Then 3.86 g product was obtained as pale yellow solid after further dryness in vacuum (90%)

¹HNMR (400 MHz, d-DMSO), 610.66 (s, 1H), 8.73 (d, J=2.0 Hz, 1H), 8.52 (d, J=1.6 Hz, 1H), 8.28 (d, J=1.6 Hz, 1H), 8.23 (s, 1H), 8.19 (s, 1H), 8.16 (d, J=7.6 Hz, 1H), 7.92 (dd, J=8.0, 1.6 Hz, 1H), 7.78 (d, J=8.4 Hz, 1H), 7.53 (d, J=8.4 Hz, 1H), 4.00 (s, 2H), 3.19 (br, 6H), 2.85 (s, 3H), 2.77 (br, 2H), 2.58 (s, 3H), 2.41 (s, 6H). MS (ESI), m/z: 533, 627

Example 42

3-(2-(1H-pyrazolo[3,4-b]pyridin-5-yl)ethynyl)-4-methyl-N-(4-((4-methylpiperazin-1-yl)methyl)-3-(trifluoromethyl)phenyl)benzamide dihydrochloride (D824 dihydrochloride)

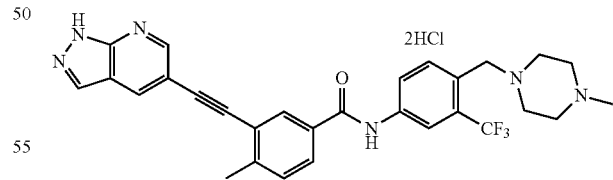

Add 3.0 g D824 (5.64 mmol) in 100 mL ethanol in a 250 mL round flask, and into hydrochloride gas is pumped into the mixture. The mixture turns clear and after stirring for 16 h, yellow solid is precipitated. The solid was collected and washed three times with ethanol and is dried in vacuum to afford 2.63 g desired product (82%).

¹HNMR (400 MHz, d-DMSO), 611.36 (br, 1H), 10.74 (s, 1H), 8.74 (d, J=2.0 Hz, 1H), 8.53 (d, J=2.0 Hz, 1H), 8.33 (d, J=1.6 Hz, 1H), 8.18-8.23 (m, 3H), 8.04 (br, 1H), 7.96 (dd,

J=8.0, 1.6 Hz, 1H), 7.54 (d, J=8.4 Hz, 1H), 4.15 (br, 2H), 3.55 (m, 6H), 3.08 (br, 2H), 2.80 (s, 3H), 2.59 (s, 3H). MS (ESI), m/z: 533

Example 43

4-methyl-N-(3-(3-methyl-1H-1,2,4-triazol-1-yl)-5-(trifluoromethyl)phenyl)-3-(2-(pyrazolo[1,5-a]pyrimidin-6-yl)ethynyl)benzamide mesylate (D818 mesylate)

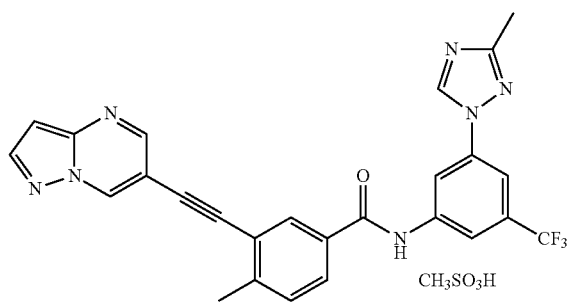

The compound was synthesized by using the procedure similar to that of Example 41.

$^1$HNMR (400 MHz, d-DMSO), δppm 10.80 (s, 1H), 9.57 (s, 1H), 9.34 (s, 1H), 8.72 (s, 1H), 8.64 (s, 1H), 8.34 (s, 1H), 8.25 (d, J=7.6 Hz, 1H), 7.98 (s, 1H), 7.55 (d, J=7.6 Hz, 1H), 6.84 (s, 1H), 2.60 (s, 3H), 2.39 (s, 3H), 2.38 (s, 3H). MS (ESI), m/z: 502

Example 44

N-(3-(1H-imidazol-1-yl)-5-(trifluoromethyl)phenyl)-4-methyl-3-(2-(pyrazolo[1,5-a]pyrimidin-6-yl)ethynyl)benzamide mesylate (D819 mesylate)

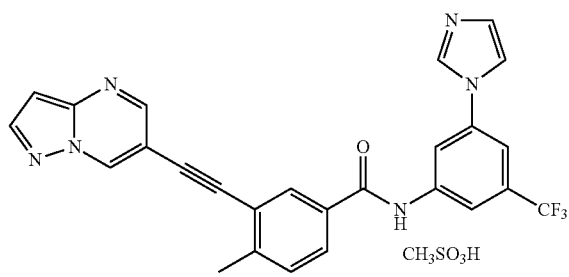

The compound was synthesized by using the procedure similar to that of Example 41.

$^1$HNMR (400 MHz, d-DMSO), 610.93 (s, 1H), 9.65 (s, 1H), 9.58 (s, 1H), 8.72 (d, J=2.0 Hz, 1H), 8.57 (s, 1H), 8.34 (d, J=2.0 Hz, 1H), 8.30 (s, 1H), 8.24 (s, 1H), 8.00 (s, 1H), 7.98 (s, 1H), 7.89 (s, 1H), 7.58 (d, J=8.0 Hz, 1H), 6.85 (s, 1H), 2.61 (s, 3H), 2.33 (s, 3H). MS (ESI), m/z: 487

Example 45

3-(2-(2-(cyclopropylamino)pyrimidin-5-yl)ethynyl)-4-methyl-N-(4-((4-methylpiperazin-1-yl)methyl)-3-(trifluoromethyl)phenyl)benzamide trimesylate (D825 trimesylate)

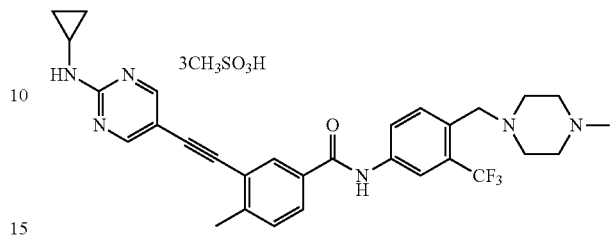

The compound was synthesized by using the procedure similar to that of Example 41.

$^1$HNMR (400 MHz, D$_2$O), δ ppm 8.23 (s, 1H), 7.89 (s, 1H), 7.71 (d, J=8.8 Hz, 1H), 7.64 (s, 1H), 7.57 (d, J=8.8 Hz, 1H), 7.52 (d, J=8.0 Hz, 1H), 7.14 (s, 1H), 4.32 (s, 2H), 3.54 (br, 8H), 2.92 (s, 3H), 2.70 (s, 9H), 2.45 (br, 1H), 2.24 (s, 3H), 1.08 (t, J=6.8 Hz, 1H), 0.78 (d, J=6.8 Hz, 2H), 0.49 (s, 2H). MS (ESI), m/z: 549, 644

Example 46

3-(2-(1H-pyrazolo[3,4-b]pyridin-5-yl)ethynyl)-4-methyl-N-(3-(3-methyl-1H-1,2,4-triazol-1-yl)-5-(trifluoromethyl)phenyl)benzamide mesylate (D835 mesylate)

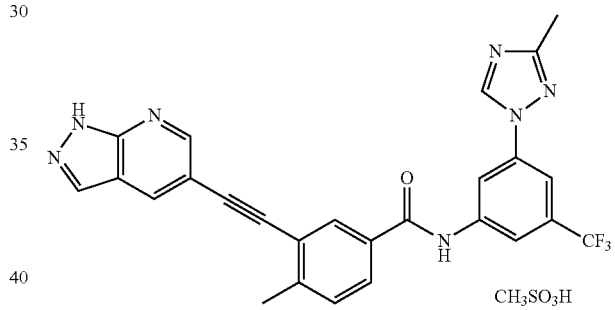

The compound was synthesized by using the procedure similar to that of Example 41.

$^1$HNMR (400 MHz, d-DMSO), δ ppm 10.78 (s, 1H), 9.37 (s, 1H), 8.73 (d, J=2.0 Hz, 1H), 8.64 (s, 1H), 8.52 (d, J=1.6 Hz, 1H), 8.22-8.27 (m, 3H), 7.97 (s, 1H), 7.94 (s, 1H), 7.52 (d, J=8.0 Hz, 1H), 2.55 (s, 3H), 2.43 (s, 3H), 2.39 (s, 3H). MS (ESI), m/z: 502

Example 47

3-(2-(1H-pyrazolo[3,4-b]pyridin-5-yl)ethynyl)-N-(3-tert-butyl-5-(4-methyl-1H-imidazol-1-yl)phenyl)-4-methylbenzamide mesylate (D968 mesylate)

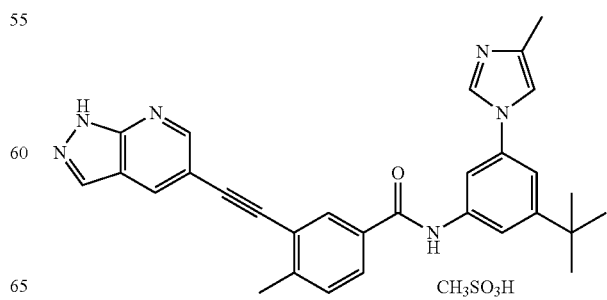

The compound was synthesized by using the procedure similar to that of Example 41.

1HNMR (400 MHz, d-DMSO), δ ppm 13.96 (s, 1H), 10.60 (s, 1H), 9.58 (d, J=1.2 Hz, 1H), 8.74 (d, J=2.0 Hz, 1H), 8.54 (d, J=2.0 Hz, 1H), 8.22-8.24 (m, 3H), 8.01 (s, 1H), 7.94 (d, J=8.0 Hz, 1H), 7.85 (s, 1H), 7.55 (d, J=8.0 Hz, 1H), 7.49 (s, 1H), 2.60 (s, 3H), 2.36 (s, 3H), 2.31 (s, 3H), 1.36 (s, 9H). MS (ESI), m/z: 489

Example 48

4-methyl-N-(4-((4-methylpiperazin-1-ylmethyl)-3-(trifluoromethyl)phenyl)-3-(2-(pyrazolo[1,5-a]pyrimidin-6-yl)ethynyl)benzamide dimesylate (D856 dimesylate)

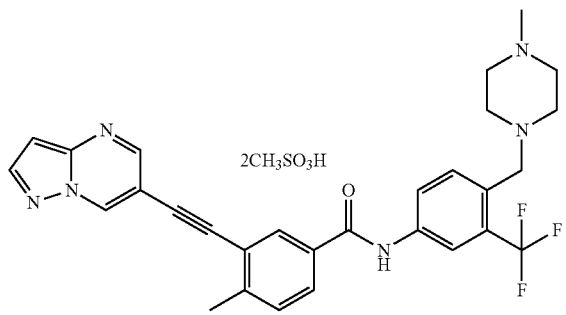 [SMILES: Cc1ccc(C(=O)Nc2ccc(CN3CCN(C)CC3)c(C(F)(F)F)c2)cc1C#Cc1cnc2ccnn2c1 ; "2CH3SO3H"]

The compound was synthesized by using the procedure similar to that of Example 41.

1HNMR (400 MHz, d-DMSO), δ ppm 10.63 (S, 1H) 9.58 (s, 1H), 8.72 (d, J=2.0 Hz, 1H), 8.34 (d, J=2.0 Hz, 1H), 8.25 (d, J=2.0 Hz, 1H), 8.20 (d, J=2.0 Hz, 1H), 8.14 (d, J=8.8 Hz, 1H), 7.97 (d, J=8.0 Hz, 1H), 7.75 (d, J=8.4 Hz, 1H), 7.55 (d, J=8.0 Hz, 1H), 6.85 (d, J=1.6 Hz, 1H), 3.82 (s, 2H), 3.41-3.47 (m, 4H), 3.07-3.23 (m, 4H), 2.83 (s, 3H), 2.60 (s, 3H), 2.36 (s, 6H). MS (ESI), m/z: 533, 627

Example 49

The heterocyclic alkynyl benzene compounds at different concentrations ($1\times10^{-10}$~$1\times10^{-5}$M) were incubated for 72 hours individually applied to 6 cell lines K562 (human CML cell line), MOLT-4 (human ALL cell line), U937 (human CML cell line), MEG-01 (human CML cell line), L78 (human lung cancer cell line), Ba/F3-T315I (mice Pro-B cells transformed with Bcr-AblT315I and STI57'-resistant cell line). After incubation for 72 hrs, cell proliferation was then determined by MTT assay or CCK8 assay, and 4 hr incubation is further conducted, the absorbance at 570 nm (CCK8, 450 nm, 650 nm) was measured using enzyme Microplate Reader. The results showed that treatment of the heterocyclic alkynyl benzene compounds could obviously decrease absorption of MTT by all different cells and significantly inhibit the proliferation of the cells mentioned above, especially K562 cells (human CML line) and Ba/F3T315I (mice Pro-B cells transformed with Bcr-AblT315I and STI57'-resistant), and the inhibition was dose-dependent. Based on the inhibition potency of the heterocyclic alkynyl benzene compounds on the cell proliferation, $IC_{50}$ values were calculated and summarized in the Table 1 and Table 2 (The compounds used were synthesized by Examples 1-40, and the compounds are marked with Drug No. series in Table 1).

TABLE 1

$IC_{50}$ values of part of the compounds on the tumor cell proliferation. (The unit is μM if no indication).

| Drug No. | K562 (human chronic myelogenous leukemia cell line) | MOLT-4 (Human acute lymphoblastic leukemia cell line | U937 Cell line | MEG-01 (Human megakaryoblastic leukaemia cell line) | K562R cells | BAF3-T315I cells | L78 (Lung cancer cell line) |
|---|---|---|---|---|---|---|---|
| D729 | 2.09 nM | 5.75 | | 6.58 | 0.07269 | 0.04968 | |
| D747 | 2.6 nM | >10 | 11.54 | 7.537 | 0.096 | 0.09973 | 10.57 |
| D752 | 0.003477 | 12.67 | 8.988 | 22.6 | 0.84 | 1.027 | >10 |
| D755 | 7.595 nM | >10 | >10 | >10 | 0.22 | 0.06097 | 11.76 |
| D767 | 0.2081 nM | >100 nM | >100 nM | >100 nM | 0.089 | 0.00424 | 11.77 nM |
| D768 | 2.597 nM | >100 nM | >100 nM | >100 nM | 0.16 | 5.993 | >100 nM |
| D770 | 99.51 nM | >100 nM | >100 nM | 3684 nM | 0.16 | 5.993 | >100 nM |
| D771 | 128.6 nM | | | | 1735 | >10 | >100 nM |
| D797 | >100 nM | >10 nM | >100 nM | >100 nM | 3.366 | 12.95 | |
| D798 | 33.99 nM | >10 nM | >100 nM | >100 nM | 1.222 | 1.864 | |
| D799 | 36.2 nM | >100 nM | >100 nM | >100 nM | 0.6118 | >10 | |
| D800 | 1.097 nM | >100 nM | >100 nM | >100 nM | 0.08966 | 0.09979 | |
| D801 | 141.3 nM | >100 nM | >100 nM | 563806 nM | 0.9063 | 10.45 | |
| D803 | 1.517 nM | 132 nM | 147.1 nM | >100 nM | 0.06333 | 0.1245/0.08580 | |
| D806 | >100 nM | >100 nM | 147.3 nM | 131.3 nM | | 1.894 | |
| D807 | 128.5 nM | >100 nM | 126.3 nM | >100 nM | 14.14 | 13.45 | |
| D809 | >100 nM | >100 nM | >100 nM | 114.9 nM | 0.1769 | 0.1022/0.07115 | |
| D818 | 1.383 nM | >100 nM | >100 nM | 210.1 nM | 0.1423 | 0.3936 | |
| D819 | 1.504 nM | 145.8 nM | 2208 nM | 122 nM | 0.1456 | 3.12 | |
| D820 | 1.374 nM | 134.3 nM | >100 nM | >100 nM | 0.03518 | 0.2763 | |
| D821 | 0.7241 nM | >100 nM | | | 0.058 | 0.01948 | |
| D822 | 4.343 nM | >100 nM | | | 0.58 | 1.104 | |
| D823 | >100 nM | >100 nM | | | 9.63 | >10 | |
| D824 | 0.4941 nM | >100 nM | | | 0.014 | 0.001645 | |
| D825 | 1.882 nM | 92.89 nM | | | 0.05 | 0.0157 | |
| D827 | 2.683 nM | 1851 nM | | | 0.059 | 0.0298 | |
| D828 | 30.93 nM | >100 nM | | | 3.07 | 2.477 | |
| D831 | 0.4661 nM | | 7134 nM | | 0.054 | 0.0368 | |
| D832 | 7.273 nM | >100 nM | | | 0.2 | 0.02184 | |

TABLE 1-continued

IC$_{50}$ values of part of the compounds on the tumor cell proliferation. (The unit is μM if no indication).

| Drug No. | K562 (human chronic myelogenous leukemia cell line) | MOLT-4 (Human acute lymphoblastic leukemia cell line) | U937 Cell line | MEG-01 (Human megakaryoblastic leukaemia cell line) | K562R cells | BAF3-T315I cells | L78 (Lung cancer cell line) |
|---|---|---|---|---|---|---|---|
| D834 | 8.703 nM | | >100 nM | | 0.19 | 0.2151 | |
| D835 | 0.4018 nM | | >100 nM | | 0.026 | 0.008578 | |
| D855 | 0.03455 | >10 | 7.167 | | 1.02 | 1.84 | |
| D856 | 0.00224 | 0.4994 | 2.001 | | 0.067 | 0.0108 | |
| D931 | >10 | 7.429 | 4.596 | | 0.51 | 2.754 | |
| D940 | 0.0657 | 0.9548 | 0.7154 | | 0.032 | 0.2447 | |
| D941 | 0.002341 | 0.3397 | 0.6959 | | 0.41 | 0.1022 | |
| D942 | 0.003542 | 0.6737 | 1.298 | | 0.04404 | 0.1016 | |
| D943 | 0.008305 | 1.626 | 2.121 | | 0.3197 | 0.6183 | |
| D963 | 0.0009975 | | >1 | | 0.07505 | 0.2426 | |
| D964 | 0.0009378 | | >1 | | 0.032 | 0.02423 | |
| D965 | 0.0005879 | | 0.8171 | | 0.0057 | 0.006867 | |
| D966 | 0.0003239 | | 0.01854 | | | 0.01381 | |
| D967 | 0.000314 | | 5.832 | | 0.2066 | 0.7981 | |
| D968 | 0.0007014 | | >1 | | 0.032 | 0.006362 | |

Note:
K562R: imatinib-resistant cell line, and was obtained by the patent applicants themselves through induction, and this cell line can be guaranteed to be released within 20 years since the date of the application.
Ba/F3-T315: Ba/F3 cell line stably expressing BCR/ABL (mutation of T315I). This cell line was obtained by the patent applicants themselves and can be guaranteed to be released within 20 years since the date of the application.

TABLE 2

IC$_{50}$ (μM) value of part of the compound on the cell proliferation of Ba/F3 cells (carrying mutation of T315I Bcr-Abl and STI571-resistant).

| Drug No. | Ba/F3 (T315I) |
|---|---|
| D729 | <0.1 |

Example 50

Figure 2:
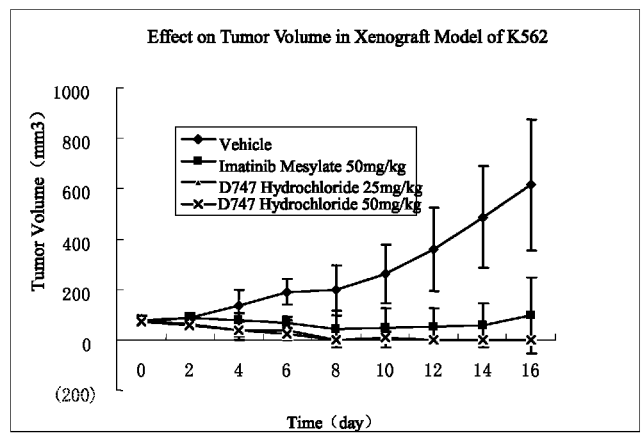
FIG. 2 is the schematic diagram of effect of compound D747 Hydrochloride (po,qd) on tumor volume in Xenograft model of K562 in Example 1.
Figure 3:
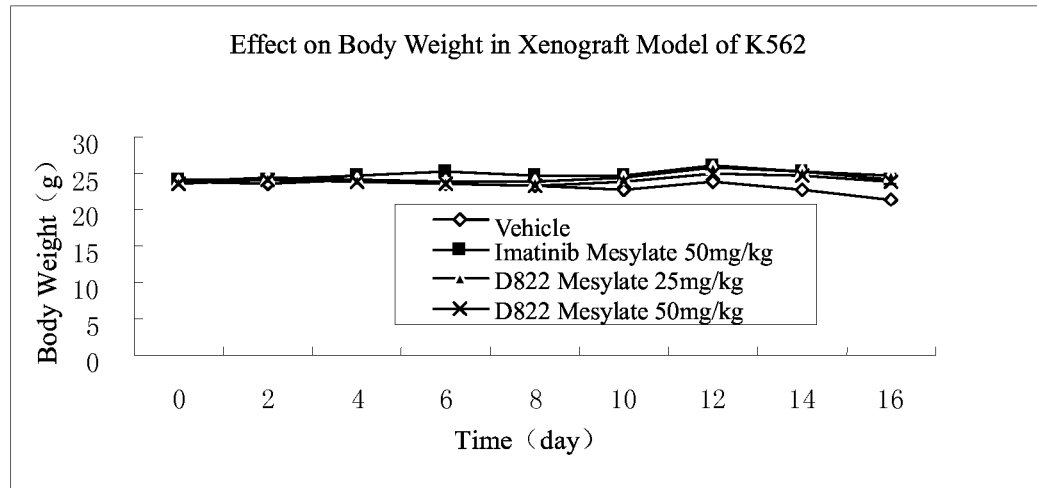
FIG. 3 is the schematic diagram of effect of compound D822 Mesylate (po,qd) on body weight in Xenograft model of K562 in Example 21.
Figure 4:
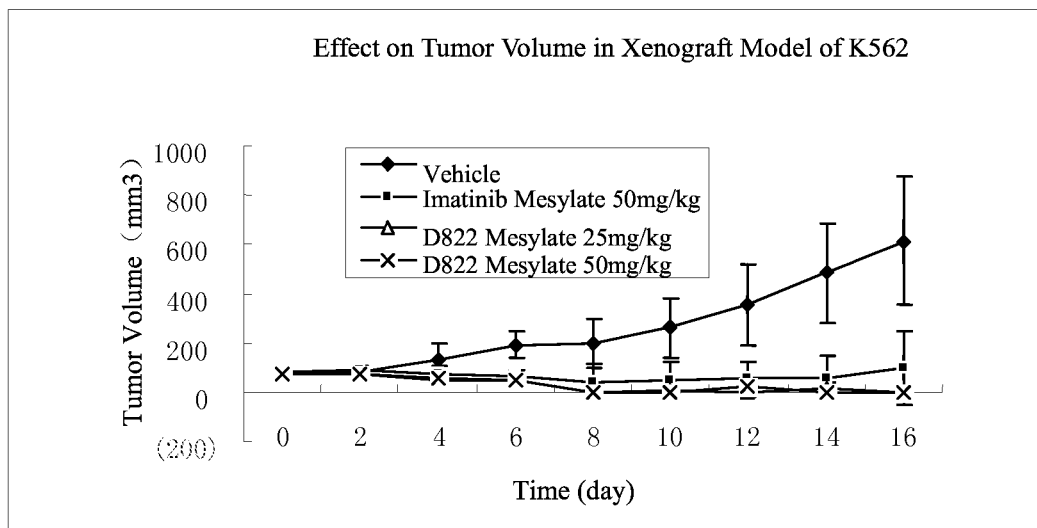
FIG. 4 is the schematic diagram of effect of compound D822 Mesylate (po,qd) on tumor volume in Xenograft model of K562 in Example 21.
Figure 5:
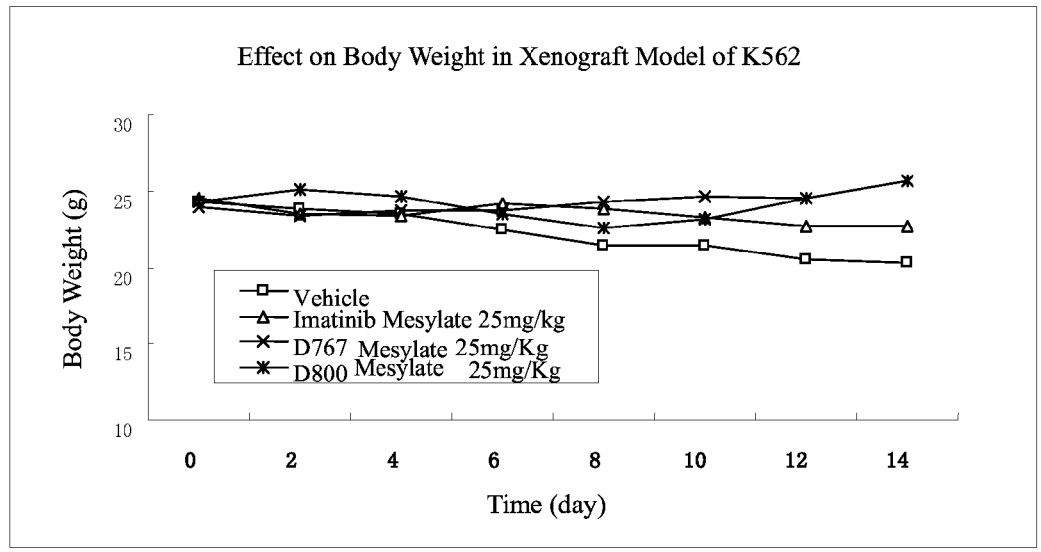
FIG. 5 is the schematic diagram of effect of compound D767 Mesylate (po,qd) and compound D800 Mesylate (po, qd) on body weight in Xenograft model of K562 in Example 17.
Figure 6:
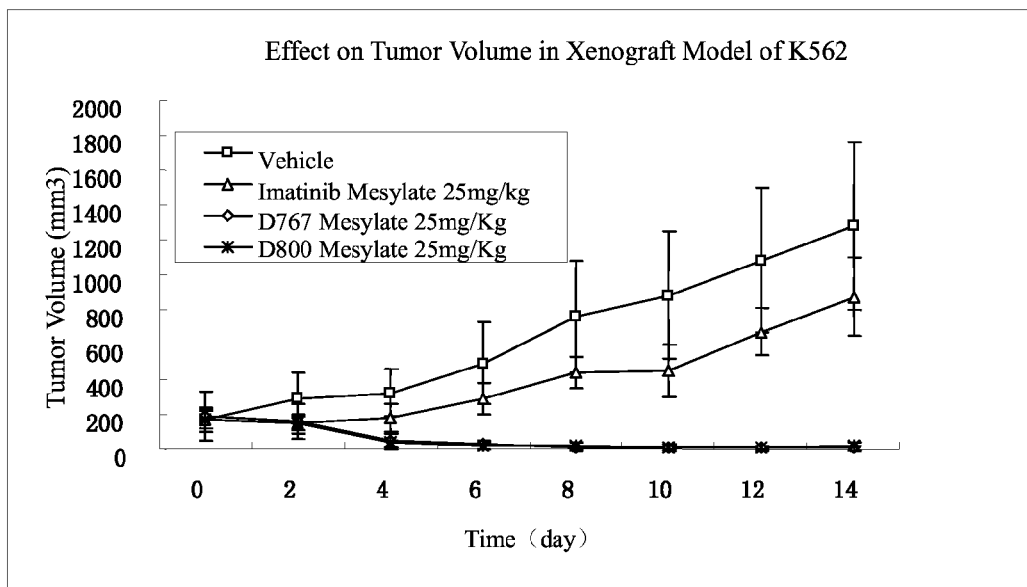
FIG. 6 is the schematic diagram of effect of compound D767 Mesylate (po,qd) and compound D800 Mesylate (po, qd) on tumor volume in Xenograft model of K562 in Example 17.
Figure 7:
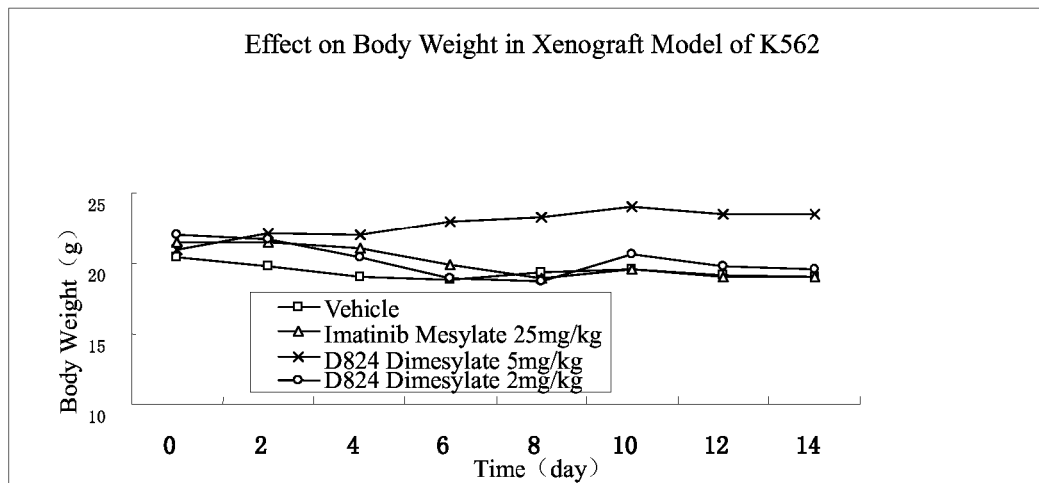
FIG. 7 is the schematic diagram of effect of compound D824 Mesylate (po,qd) on body weight in Xenograft model of K562 in Example 41.
Figure 8:
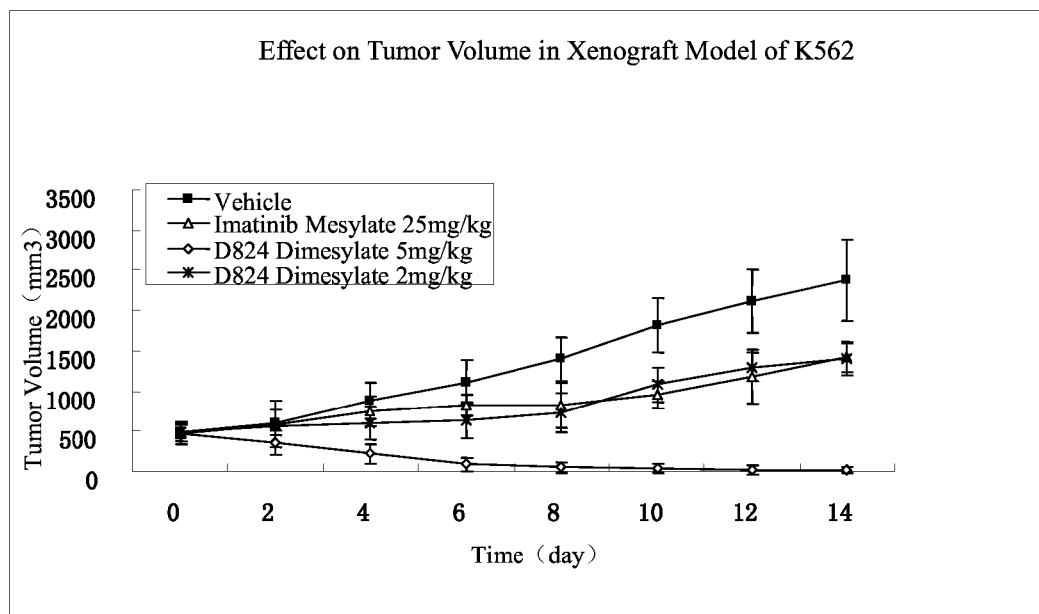
FIG. 8 is the schematic diagram of effect of compound D824 Mesylate (po,qd) on tumor volume in Xenograft model of K562 in Example 41.

K562 cells (human CML cell line expressing native Bcr-Abl) were inoculated into the right flank of each BALB/C-nu nude mouse (5×106 cells/mouse), and when the mean tumor volume reached 100-200 mm³, mice were grouped and administrated orally. The doses for each compound varied within the range of 0, 2, 5, 25 and 50 mg/kg/, po, qd, and each group had 8~10 mice. Tumor volume and body weight were monitored once every 2 days (In each group, the tumor volume and body weight at beginning of the day were recorded). Tumor volume was calculated as λ/6*a*b*b.L×W2/2 (a and b are the length and width of the tumor, respectively). The data showed that the hydrochloride form of D747, mesylate form of D822, D767, D800 and dimethylate form of D824 did not cause the body weight loss. These compounds showed good anti-tumor activities and the body weight gain could be observed at the effective doses of these compounds. The hydrochloride form of D747, mesylate forms of D822, D767, D800 and dimethylate form of D824 could completely inhibit the tumor growth at the dose of 25, 25, 25, 25 and 5 mg/kg, respectively, and they could eradicate the tumor cells and heal the tumor. The hydrochloride form of D747 and mysylate form of D822 showed better anti-tumor effect than imatinib. The results were shown in Drawings as FIGS. 1, 2, 3, 4, 5, 6, 7 and 8.

Example 51

Figure 9:
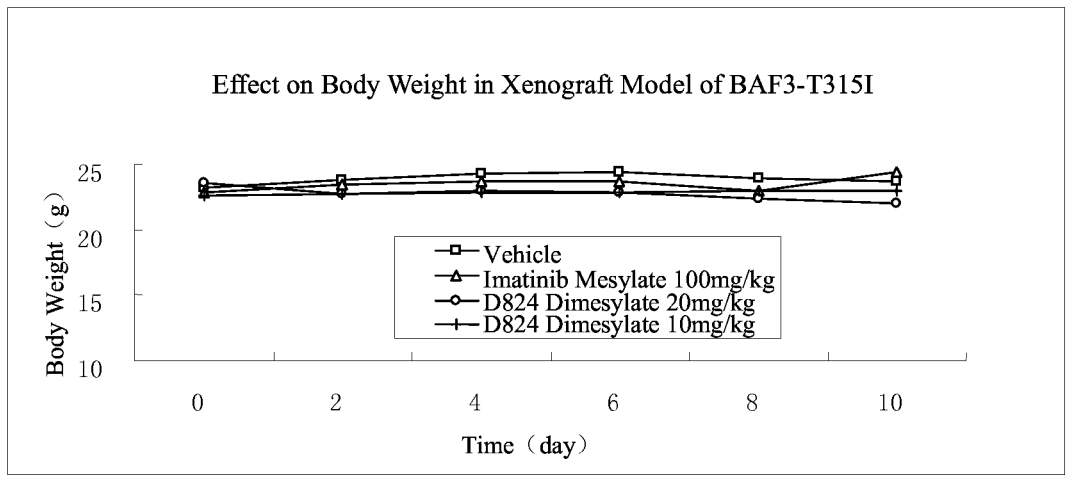
FIG. 9 is the schematic diagram of effect of compound D824 Mesylate (po,qd) on body weight in Xenograft model of BAF3-T315I in Example 41.
Figure 10:
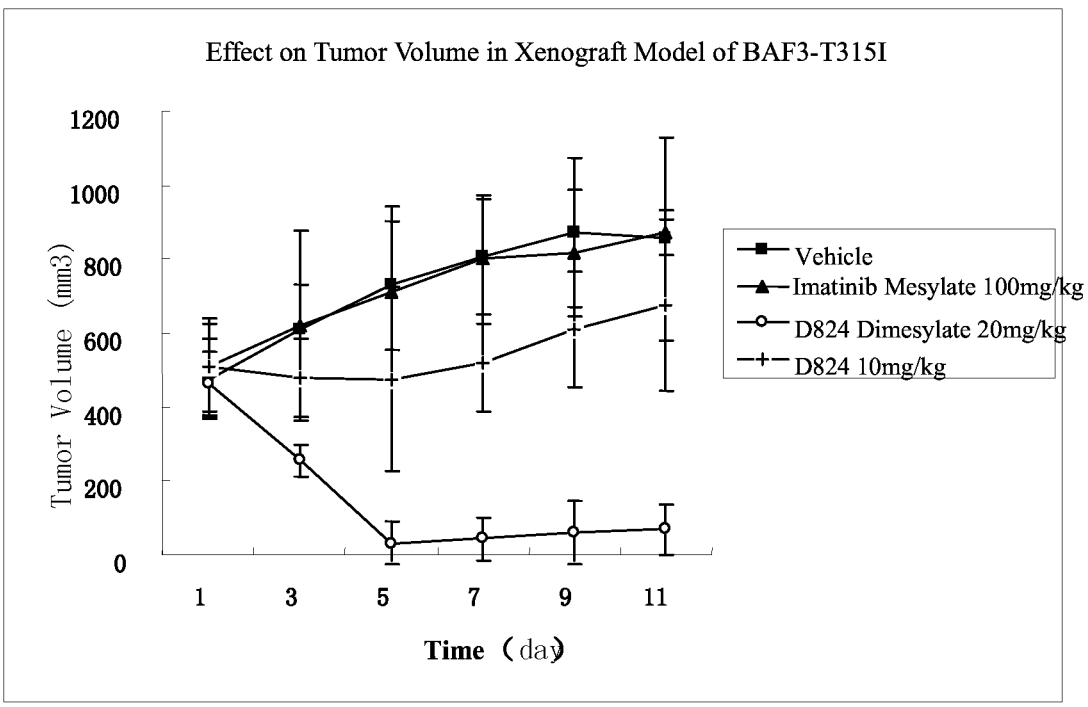
FIG. 10 is the schematic diagram of effect of compound D824 Mesylate (po,qd) on tumor volume in Xenograft model of BAF3-T315I in Example 41.
Figure 11:
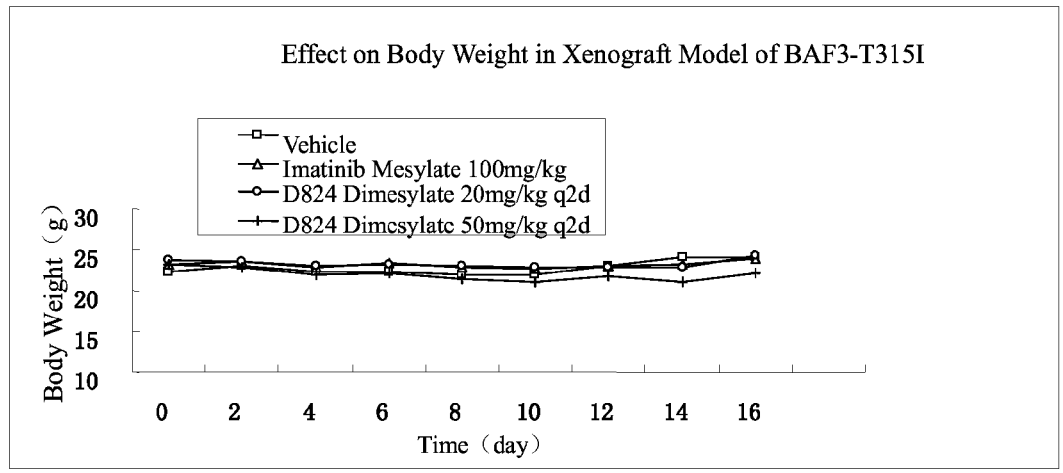
FIG. 11 is the schematic diagram of effect of compound D824 Mesylate (po,q2d) on body weight in Xenograft model of BAF3-T315I in Example 41.
Figure 12:
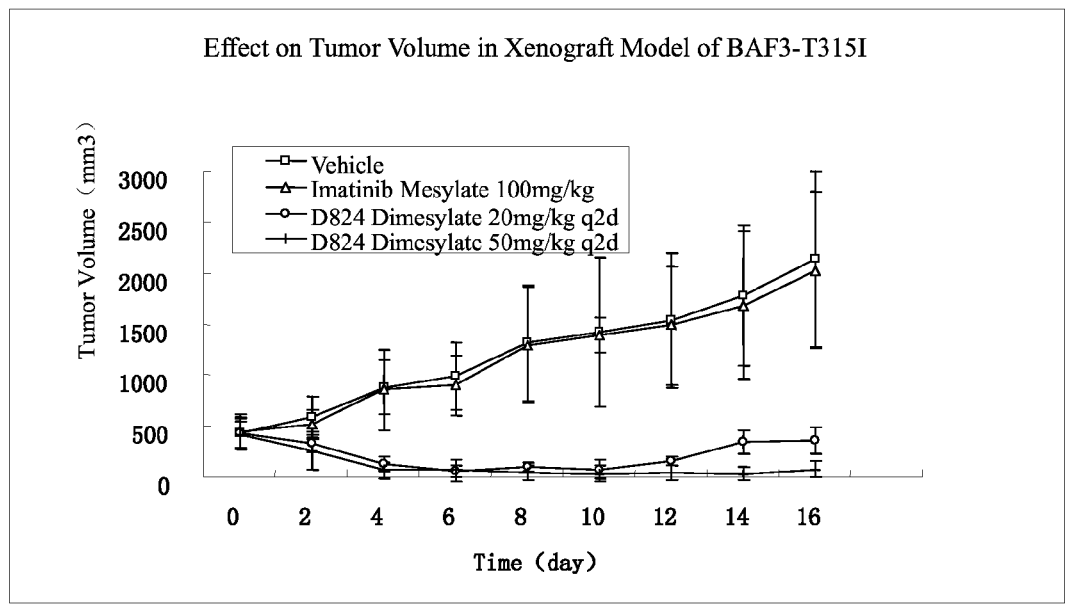
FIG. 12 is the schematic diagram of effect of compound D824 Mesylate (po,q2d) on tumor volume in Xenograft model of BAF3-T315I in Example 41.
Figure 13:
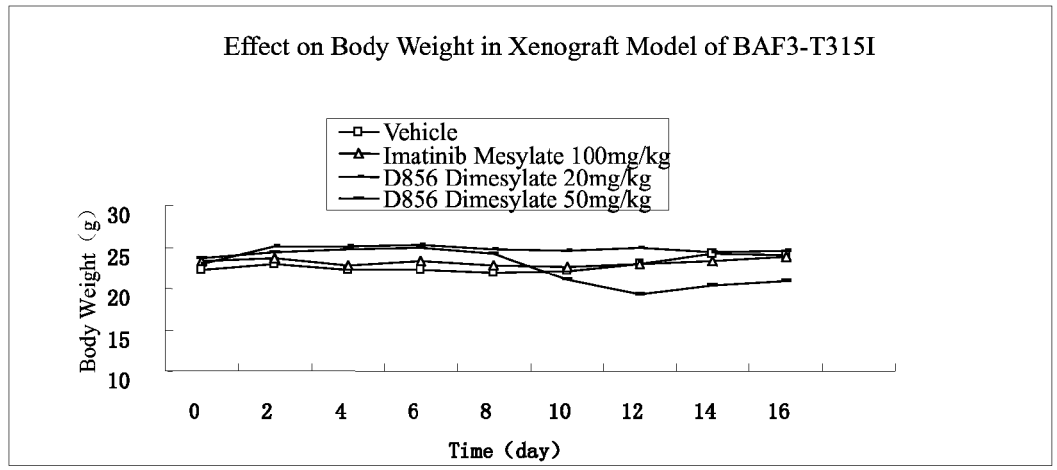
FIG. 13 is the schematic diagram of effect of compound D856 Mesylate (po,qd) on body weight in Xenograft model of K562 in Example 48.
Figure 14:
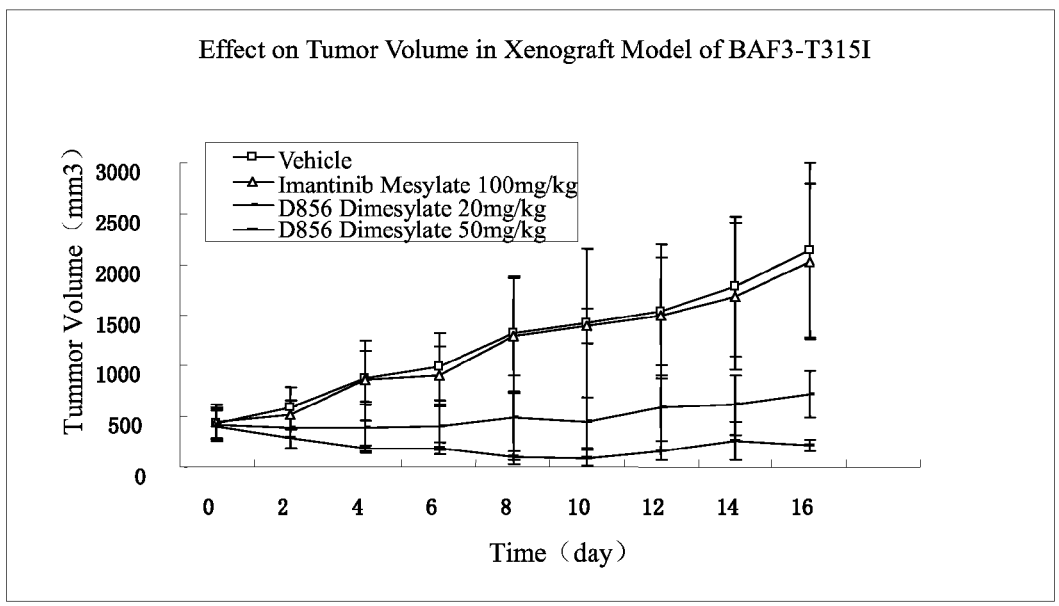
FIG. 14 is the schematic diagram of effect of compound D856 Mesylate (po,qd) on tumor volume in Xenograft model of K562 in Example 48.
Figure 15:
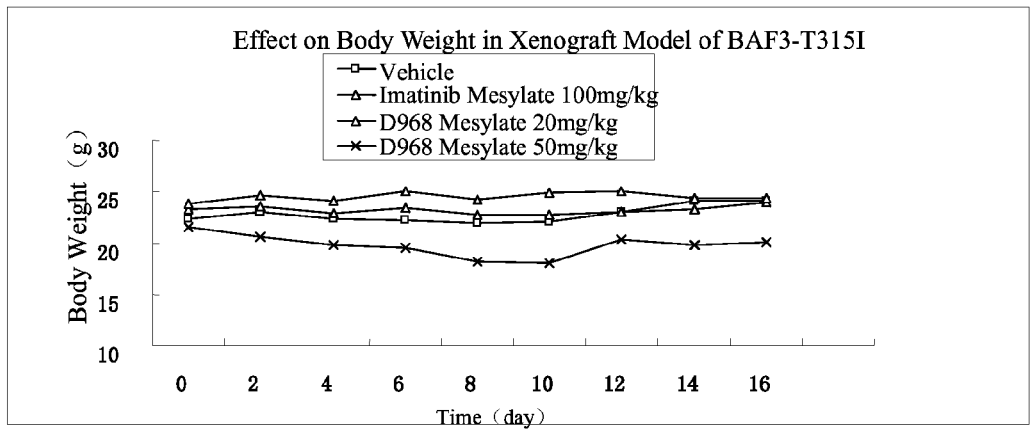
FIG. 15 is the schematic diagram of effect of compound D968 Mesylate (po,qd) on body weight in Xenograft model of K562 in Example 34.
Figure 16:
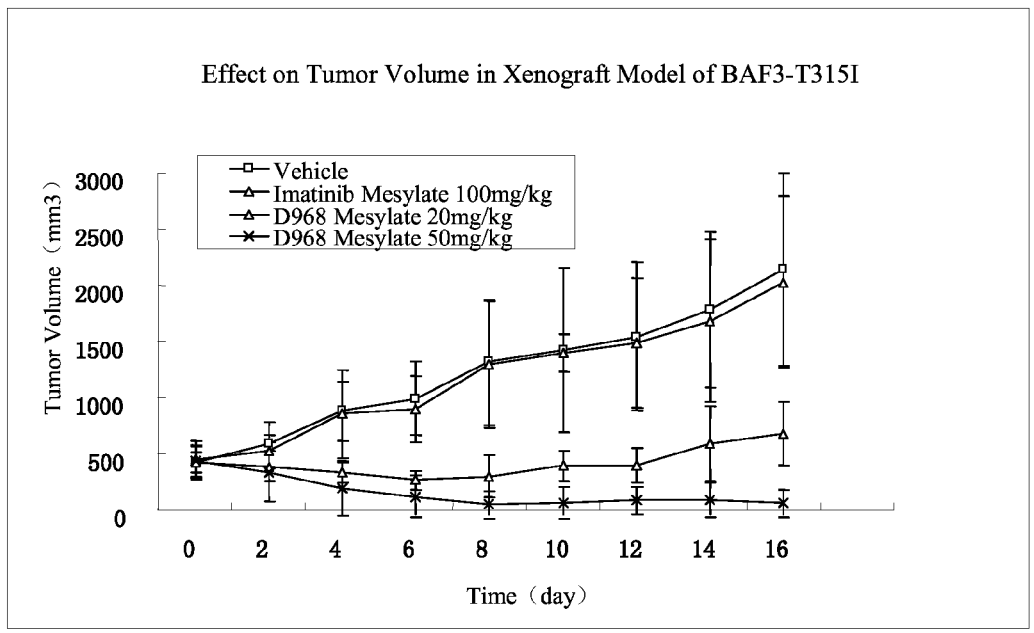
FIG. 16 is the schematic diagram of effect of compound D968 Mesylate (po,qd) on tumor volume in Xenograft model of K562 in Example 34.

Ba/F3-Bcr/ABL-T315Icells were inoculated into the right flank of each SCID nude mouse (2×106 cells/mouse). When the mean tumor volume reached 300-500 mm³, mice were grouped and administered orally. Different dosage group and administration intervals were set, 50 mg/kg, 20 mg/kg, and 10 mg/kg po, q2d or qd, and each group had 8~10 mice. Tumor volume and body weight were monitored once every 2 days (In each group, the tumor volume and body weight at beginning of the day were recorded). Tumor volume was calculated as π/6*a*b*b.L×W2/2 (a and b are the length and width of the tumor, respectively). The data showed that the dimesylate form of D824 at the dose of 25 mg/kg, po, q2d or qd could help the body weight gain and almost completely suppressed the tumor growth. The dimesylate forms of D856 and methylate form of D968 could inhibit the tumor growth at the dose of 20 mg/kg, po, q2d or qd. The results were shown in Drawings as FIG. 9, 10, 11, 12, 13, 14, 15, 16.

Example 52

Pharmacokinetics and bioavailability in rats. SD rats (2 males and 2 females) were administrated once through oral gavage (25 mg/kg) or through intravenous injection (2.5~10 mg/kg), respectively. The blood samples were collected at the proper time points after administration, add heparin-anticoagulant, and the supernatants of the blood samples were collected (3000 rpm, 10 min) and stored at −20° C. for HPLC-MS analysis. After protein-precipitation procedure with acetonitrile, supernatants were collected after 3000 rpm, 10 min for analysis with HPLC-MS. The data were analyzed with software DAS2.0 to separately acquire the parameters of compartment models and non-compartment models. The bioavailability was calculated according to AUC data. The corresponding pharmaceutical acceptable salt forms of the compounds D747, D752, D755, D767, D800, D822, D824, D831, D856 and D825 had adequate pharmacokinetics parameters and they are suitable for further in vivo pharmacodynamic study. The results are summarized in Table 3.

TABLE 3

Pharmacokinetics data of some of the compounds.

| | Administration route | Animal Number | Dose level mg/kg | AUC(0-∞) ug/L*h | Cmax ug/l | T1/2 (Hr) | Tmax (Hr) | BA(% Oral bioavailability) |
|---|---|---|---|---|---|---|---|---|
| D747 | PO | ♀2 ♂2 | 25 | 251684.381 | 6205 | 48.701 | 4.5 | 35.3 |
| hydrochloride salt | IV | ♀2 ♂2 | 10 | 285187.275 | 49750 | 71.753 | 0.033 | |
| D822 mesylate | PO | ♀2 ♂2 | 25 | 10736.39 | 814 | 8.04 | 3 | 31.2 |
| salt | IV | ♀2 ♂2 | 10 | 13754.54 | 23056.25 | 3.15 | 0.033 | |
| D752 mesylate | PO | ♀2 ♂2 | 20 | 70411.149 | 1900 | 7.548 | 20 | 11.54 |
| salt | IV | ♀2 ♂2 | 10 | 304881.256 | 19606.25 | 43.854 | 0.033 | |
| D800 | PO | ♀2 ♂2 | 5 | 35809.5 | 10975 | 7.5 | 0.033 | 27.1 |
| hydrochloride salt | IV | ♀2 ♂2 | 25 | 48574.3 | 3090 | 7.8 | 2 | |
| D767 | PO | ♀2 ♂2 | 25 | 62208 | 3615 | 7.179 | 7.75 | 19 |
| hydrochloride salt | IV | ♀2 ♂2 | 5 | 65534 | 15319 | 5.596 | 0.033 | |
| D755 | PO | ♀2 ♂2 | 25 | 23700 | 1255 | 8.298 | 6.25 | 63.3 |
| hydrochloride salt | IV | ♀2 ♂2 | 2.5 | 3745 | 510 | 26.181 | 0.033 | |
| D648 | PO | ♂4 | 25 | 1471.701 | 509.25 | 1.117 | 1 | 10.9 |
| hydrochloride salt | IV | ♂4 | 5 | 2694.862 | 2602.5 | 3.01 | 0.183 | |
| D856 dimesylate | PO | ♂4 | 25 | 31829.108 | 899.5 | 22.199 | 6.5 | 78 |
| salt | IV | ♂4 | 5 | 8165.792 | 934.375 | 19.97 | 0.033 | |
| D753 mesylate | PO | ♂4 | 25 | 1080.493 | 147.05 | 18.275 | 4 | 1.6 |
| salt | IV | ♂4 | 5 | 13128.922 | 7418.75 | 58.193 | 0.083 | |
| D680 mesylate | PO | ♀2 ♂2 | 50 | 4847.264 | 862 | 2.728 | 2 | 8.7 |
| salt | IV | ♀2 ♂2 | 10 | 11175.59 | 14168.75 | 3.699 | 0.033 | |
| D824 | PO | ♂4 | 25 | 7108.253 | 390.5 | 10.55 | 6 | 48.7 |
| hydrochloride salt | IV | ♂4 | 5 | 2922.411 | 1375.625 | 5.557 | 0.067 | |
| D767 mesylate | PO | ♂4 | 25 | 27850.615 | 2322.5 | 5.949 | 2.75 | 9.4 |
| salt | IV | ♂4 | 5 | 59222.45 | 14093.75 | 4.471 | 0.033 | |
| D835 | PO | ♂4 | 25 | 3467.961 | 233 | 8.813 | 4 | 8.1 |
| hydrochloride salt | IV | ♂4 | 5 | 8536.548 | 975.625 | 16.863 | 0.033 | |
| D831 mesylate | PO | ♂4 | 25 | 73862.101 | 9515 | 4.665 | 2.25 | 13.8 |
| salt | IV | ♂3 | 5 | 107229.516 | 64250 | 5.237 | 0.033 | |
| D824 dimesylate | PO | ♂4 | 25 | 12628.23 | 774.75 | 8.72 | 4.25 | 58.7 |
| salt | IV | ♂4 | 5 | 4304.444 | 2235.625 | 6.098 | 0.033 | |
| D825 mesylate | PO | ♂4 | 25 | 34561.045 | 1700 | 11.492 | 4.75 | 58.5 |
| salt | IV | ♂4 | 5 | 11819.424 | 2331.25 | 11.693 | 0.033 | |

The above description is the detail and specific explanation for embodiments of the present invention, but it cannot be understood as the restrictions on the scope of the present invention. It should be noted that one having ordinary skill in the art would make many equivalent modification and improvement within spirit of the present invention, which should be included in the protection scope of the present invention.

The invention claimed is:

1. A heterocyclic alkynyl benzene compound having formula (I),

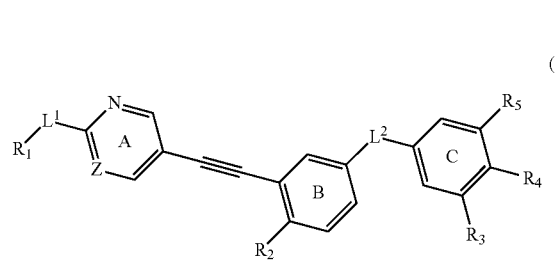

or a pharmaceutically acceptable salt, prodrug, or stereoisomer thereof, wherein:

$R_1$ together with $L^1$, the carbon to which $L^1$ is attached, Z and ring A form a moiety having the structure

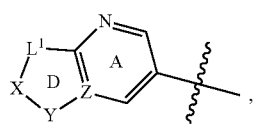

wherein the moiety is selected from the group consisting of

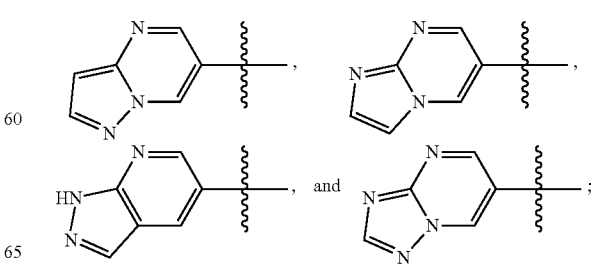

L² is —CONH— or —NHCO—;
R₂ is
  1) H;
  2) Halogen;
  3) $C_1$~$C_5$ alkyl;
  4) $C_3$~$C_6$ cycloalkyl; or
  5) $C_1$~$C_5$ alkyl substituted with one or more F atoms;
R₃ is
  1) H;
  2) Halogen;
  3) $C_1$~$C_4$ alkyl;
  4) $C_3$~$C_6$ cycloalkyl; or
  5) $C_1$~$C_4$ alkyl substituted with one or more F atoms;
R₅ is H, provided that R₄ is
  1) H;
  2) $(CH_2)_n NR_6 R_7$; or
  3) $(CH_2)_n$-Het¹; or
R₄ is H, provided that R₅ is
  1) H; or
  2) Het²;
wherein n is 0 or 1;
Het¹ is a nonaromatic heterocycle containing 1 to 3 N atoms; Het² is an aromatic five-membered heterocycle containing 1 to 3 heteroatoms independently selected from the group consisting of N, O and S; wherein any C or N position of Het¹ and Het² is optionally substituted with alkyl, cycloalkyl or $NR_6 R_7$;
each R₆ and R₇ is independently
  1) H;
  2) $C_1$~$C_3$ alkyl;
  3) $C_1$~$C_3$ alkyl substituted with one or more F atoms; or
  4) $C_3$~$C_6$ cycloalkyl; or
R₆ and R₇ together with the N atom to which they are attached form a penta-, hexa-, hepta- or octatomic ring, wherein the penta-, hexa-, hepta- or octatomic ring optionally further contains an O or S atom.

2. The heterocyclic alkynyl benzene compound of claim 1, or a pharmaceutically acceptable salt, prodrug, or stereoisomer thereof, wherein:
R₂ is
  1) H
  2) methyl, ethyl, isopropyl, tert-butyl;
  3) cyclopropyl;
  4) F, Cl, Br; or
  5) CF₃.

3. The heterocyclic alkynyl benzene compound of claim 1, or a pharmaceutically acceptable salt, prodrug, or stereoisomer thereof, wherein:

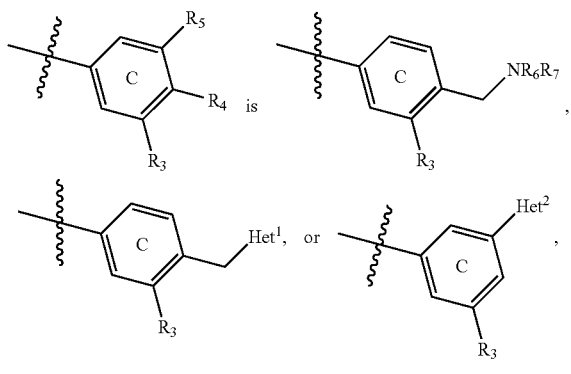

Het² is substituted imidazole, substituted pyrazole, substituted oxazole, substituted triazole, substituted oxazolidine, or substituted thiazole.

4. The heterocyclic alkynyl benzene compound of claim 1, or a pharmaceutically acceptable salt, prodrug, or stereoisomer thereof, wherein the compound is

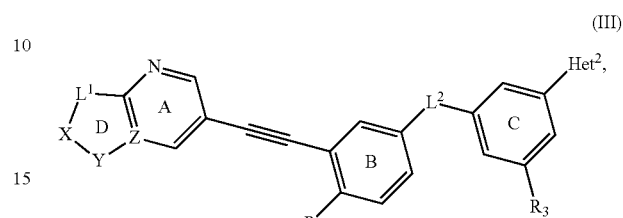

(III)

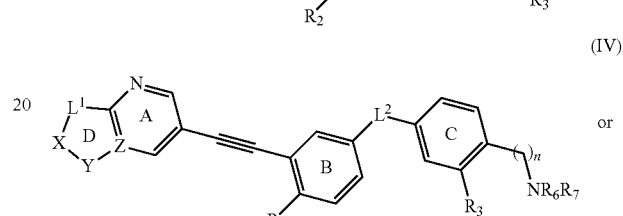

(IV)

or

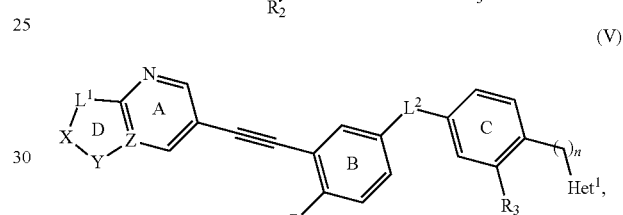

(V)

or a pharmaceutically acceptable salt, prodrug, or stereoisomer thereof.

5. The heterocyclic alkynyl benzene compound of claim 4, or a pharmaceutical acceptable salt, prodrug, or stereoisomer thereof, wherein the heterocyclic alkynyl benzene compound is selected from the group consisting of:

4-methyl-N-(4-((4-methylpiperazin-1-yl)methyl)-3-(trifluoromethyl)phenyl)-3-(2-(pyrazolo[1,5-a]pyrimidin-6-yl)ethynyl)benzamide;

N-(3-(1H-imidazol-1-yl)-5-(trifluoromethyl)phenyl)-4-methyl-3-(2-(pyrazolo[1,5-a]pyrimidin-6-yl)ethynyl)benzamide;

4-methyl-N-(3-(3-methyl-1H-1,2,4-triazol-1-yl)-5-(trifluoromethyl)phenyl)-3-(2-(pyrazolo[1,5-a]pyrimidin-6-yl)ethynyl)benzamide;

3-(2-(imidazo[1,2-a]pyrimidin-6-yl)ethynyl)-4-methyl-N-(3-(4-methyl-1H-imidazol-1-yl)-5-(trifluoromethyl)phenyl)benzamide;

3-(2-(1H-pyrazolo[3,4-b]pyridin-5-yl)ethynyl)-4-methyl-N-(3-(4-methyl-1H-imidazol-1-yl)-5-(trifluoromethyl)phenyl)benzamide;

N-(3-(1H-imidazol-1-yl)-5-(trifluoromethyl)phenyl)-3-(2-(1H-pyrazolo[3,4-b]pyridin-5-yl)ethynyl)-4-methylbenzamide;

3-(2-(1H-pyrazolo[3,4-b]pyridin-5-yl)ethynyl)-4-methyl-N-(3-(3-methyl-1H-1,2,4-triazol-1-yl)-5-(trifluoromethyl)phenyl)benzamide;

3-(2-([1,2,4]triazolo[1,5-a]pyrimidin-6-yl)ethynyl)-4-methyl-N-(3-(4-methyl-1H-imidazol-1-yl)-5-(trifluoromethyl)phenyl)benzamide;

4-methyl-N-(3-(4-methyl-1H-imidazol-1-yl)-5-(trifluoromethyl)phenyl)-3-(2-(pyrazolo[1,5-a]pyrimidin-6-yl)ethynyl)benzamide;

3-(2-(1H-pyrazolo[3,4-b]pyridin-5-yl)ethynyl)-4-methyl-N-(3-(trifluoromethyl)phenyl)benzamide;

3-(2-(1H-pyrazolo[3,4-b]pyridin-5-yl)ethynyl)-4-methyl-N-(4-((4-methylpiperazin-1yl)methyl)-3-(trifluoromethyl)phenyl)benzamide;

4-methyl-N-(4-(morpholinomethyl)-3-(trifluoromethyl)phenyl)-3-(2-(pyrazolo[1,5-a]pyrimidin-6-yl)ethynyl)benzamide;

N-(4-((4-(2-hydroxyethyl)piperazin-1-yl)methyl)-3-(trifluoromethyl)phenyl)-4-methyl-3-(2-(pyrazo[1,5-a]pyrimidin-6-yl)ethynyl)benzamide;

(S)—N-(4-((3-(dimethylamino)pyrrolidin-1-yl)methyl)-3-(trifluoromethyl)phenyl)-4-methyl-3-(2-(pyrazolo[1,5-a]pyrimidin-6-yl)ethynyl)benzamide;

N-(3-tert-butyl-5-(4-methyl-1H-imidazol-1-yl)phenyl)-4-methyl-3-(2-(pyrazolo[1,5-a]pyrimidin-6-yl)ethynyl)benzamide;

3-(2-(1H-pyrazolo[3,4-b]pyridin-5-yl)ethynyl)-4-methyl-N-(3-(4-methyl-1H-imidazol-1-yl)phenyl)benzamide;

3-(2-(1H-pyrazolo[3,4-b]pyridin-5-yl)ethynyl)-N-(3-tert-butyl-5-(4-methyl-1H-imidazol-1-yl)phenyl)-4-methylbenzamide;

3-(2-(1H-pyrazolo[3,4-b]pyridin-5-yl)ethynyl)-N-(3-fluoro-5-(4-methyl-1H-imidazol-1-yl)phenyl)-4-methylbenzamide;

3-(2-(1H-pyrazolo[3,4-b]pyridin-5-yl)ethynyl)-N-(3-chloro-5-(4-methyl-1H-imidazol-1-yl)phenyl)-4-methylbenzamide;

(R)—N-(4-((3-(dimethylamino)pyrrolidin-1-yl)methyl)-3-(trifluoromethyl)phenyl)-4-methyl-3-(2-(pyrazolo[1,5-a]pyrimidin-6-yl)ethynyl)benzamide;

(S)-3-(2-(1H-pyrazolo[3,4-b]pyridin-5-yl)ethynyl)-N-(4-((3-(dimethylamino)pyrrolidin-1-yl)methyl)-3-(trifluoromethyl)phenyl)-4-methylbenzamide;

(R)-3-(2-(1H-pyrazolo[3,4-b]pyridin-5-yl)ethynyl)-N-(4-((3-(dimethylamino)pyrrolidin-1-yl)methyl)-3-(trifluoromethyl)phenyl)-4-methylbenzamide;

3-(2-(1H-pyrazolo[3,4-b]pyridin-5-yl)ethynyl)-N-(4-((4-methylpiperazin-1-yl)methyl)-3-(trifluoromethyl)phenyl)benzamide;

3-(2-(1H-pyrazolo[3,4-b]pyridin-5-yl)ethynyl)-4-methyl-N-(4-((4-methylpiperazin-1-yl)methyl)-3-(trifluoromethyl)phenyl)benzamide bimesylate;

3-(2-(1H-pyrazolo[3,4-b]pyridin-5-yl)ethynyl)-4-methyl-N-(4-((4-methylpiperazin-1-yl)methyl)-3-(trifluoromethyl)phenyl)benzamide dihydrochloride;

methyl-N-(3-(3-methyl-1H-1,2,4-triazol-1-yl)-5-(trifluoromethyl)phenyl)-3-(2-(pyrazolo[1,5-a]pyrimidin-6-yl)ethynyl)benzamide mesylate;

N-(3-(1H-imidazol-1-yl)-5-(trifluoromethyl)phenyl)-4-methyl-3-(2-(pyrazolo[1,5-a]pyrimidin-6-yl)ethynyl)benzamide mesylate;

3-(2-(1H-pyrazolo[3,4-b]pyridin-5-yl)ethynyl)-4-methyl-N-(3-(3-methyl-1H-1,2,4-triazol-1-yl)-5-(trifluoromethyl)phenyl)benzamide mesylate;

3-(2-(1H-pyrazolo[3,4-b]pyridin-5-yl)ethynyl)-N-(3-tert-butyl-5-(4-methyl-1H-imidazol-1-yl)phenyl)-4-methylbenzamide mesylate; and 4-methyl-N-(4-((4-methylpiperazin-1-yl)methyl)-3-(trifluoromethyl)phenyl)-3-(2-(pyrazolo[1,5-a]pyrimidin-6-yl)ethynyl)benzamide dimesylate, or a pharmaceutically acceptable salt, prodrug, or stereoisomer thereof.

6. A method for treating cancer in a patient, wherein the cancer is selected from the group consisting of leukemia, gastrointestinal stromal tumors (GIST), histiocytic lymphoma, non-small cell lung cancer, small cell lung cancer, lung adenocarcinoma, cell lung carcinoma, pancreatic cancer, breast cancer, prostate cancer, liver cancer, skin cancer, squamous cell carcinoma, and nasopharyngeal carcinoma, the method comprising administering a pharmaceutical composition to the patient, wherein the pharmaceutical composition comprises a heterocyclic alkynyl benzene compound of claim 1 or a pharmaceutically acceptable salt, stereoisomer or prodrug thereof and one or more pharmaceutically acceptable carriers.

7. A method for treating cancer in a patient, wherein the cancer is selected from the group consisting of leukemia, gastrointestinal stromal tumors (GIST), histiocytic lymphoma, non-small cell lung cancer, small cell lung cancer, lung adenocarcinoma, squamous cell lung cancer, pancreatic cancer, breast cancer, prostate cancer, liver cancer, skin cancer, squamous cell carcinoma, and nasopharyngeal carcinoma, the method comprising administering a heterocyclic alkynyl benzene compound of claim 1 or a pharmaceutically acceptable salt, stereoisomer or pro-drug thereof to the patient.

8. The method of claim 6, wherein the cancer is leukemia.

9. The method of claim 8, wherein the leukemia is chronic myelogenous leukemia, acute lymphoblastic leukemia, or megakaryoblastic leukemia.

10. The method of claim 7, wherein the cancer is leukemia.

11. The method of claim 10, wherein the leukemia is chronic myelogenous leukemia, acute lymphoblastic leukemia, or megakaryoblastic leukemia.

* * * * *